US010060908B2

(12) United States Patent
Frostegård

(10) Patent No.: US 10,060,908 B2
(45) Date of Patent: Aug. 28, 2018

(54) OXIDIZED CARDIOLIPIN AS A PRO-INFLAMMATORY FACTOR

(71) Applicant: MEDIRISTA BIOTECHNOLOGIES AB, Stockholm (SE)

(72) Inventor: Johan Frostegård, Stockholm (SE)

(73) Assignee: MEDIRISTA BIOTECHNOLOGIES AB, Stockholm (SE)

( * ) Notice: Subject to any disclaimer, the term of this patent is extended or adjusted under 35 U.S.C. 154(b) by 428 days.

(21) Appl. No.: 13/964,581

(22) Filed: Aug. 12, 2013

(65) Prior Publication Data

US 2014/0363450 A1 Dec. 11, 2014

Related U.S. Application Data

(62) Division of application No. 13/140,906, filed as application No. PCT/EP2009/009199 on Dec. 21, 2009, now abandoned.

(Continued)

(51) Int. Cl.
*A61K 38/00* (2006.01)
*G01N 33/00* (2006.01)
(Continued)

(52) U.S. Cl.
CPC ..... *G01N 33/5308* (2013.01); *A61K 38/1709* (2013.01); *C07K 16/18* (2013.01); *C07K 16/44* (2013.01); *G01N 33/564* (2013.01); *G01N 33/92* (2013.01); *C07K 2317/76* (2013.01); *G01N 2800/104* (2013.01); *G01N 2800/24* (2013.01); *G01N 2800/2871* (2013.01);
(Continued)

(58) Field of Classification Search
CPC .. G01N 33/5308; G01N 33/92; G01N 33/564; C07K 16/18; C07K 16/44; A61K 38/1709
See application file for complete search history.

(56) References Cited

U.S. PATENT DOCUMENTS 4,439,196 A  3/1984 Higuchi
4,447,224 A  5/1984 Decant et al.
(Continued)

FOREIGN PATENT DOCUMENTS

WO  WO 00/35436  6/2000
WO  WO 02/067857  9/2002
(Continued)

OTHER PUBLICATIONS

Tuominen et al., (Arteriosclerosis, Thrombosis, and Vascular Biology. Sep. 2006. 29(9):2096-2102).*
(Continued)

*Primary Examiner* — Cherie M Stanfield
(74) *Attorney, Agent, or Firm* — Parker Highlander PLLC

(57) ABSTRACT

Low levels of antibodies reactive with oxidized Cardiolipin (oxCL) in mammals are related to an increased risk of developing cardiovascular diseases, auto-immune diseases or inflammatory conditions. High levels can have a protective function and in general there is a negative association between manifestations of these conditions and antibodies against oxCL. Thus, based on their relations methods of monitoring, determining and diagnosing as well as methods of immunization and therapy of these diseases and conditions are provided.

18 Claims, 26 Drawing Sheets

Related U.S. Application Data

Figure 1A:
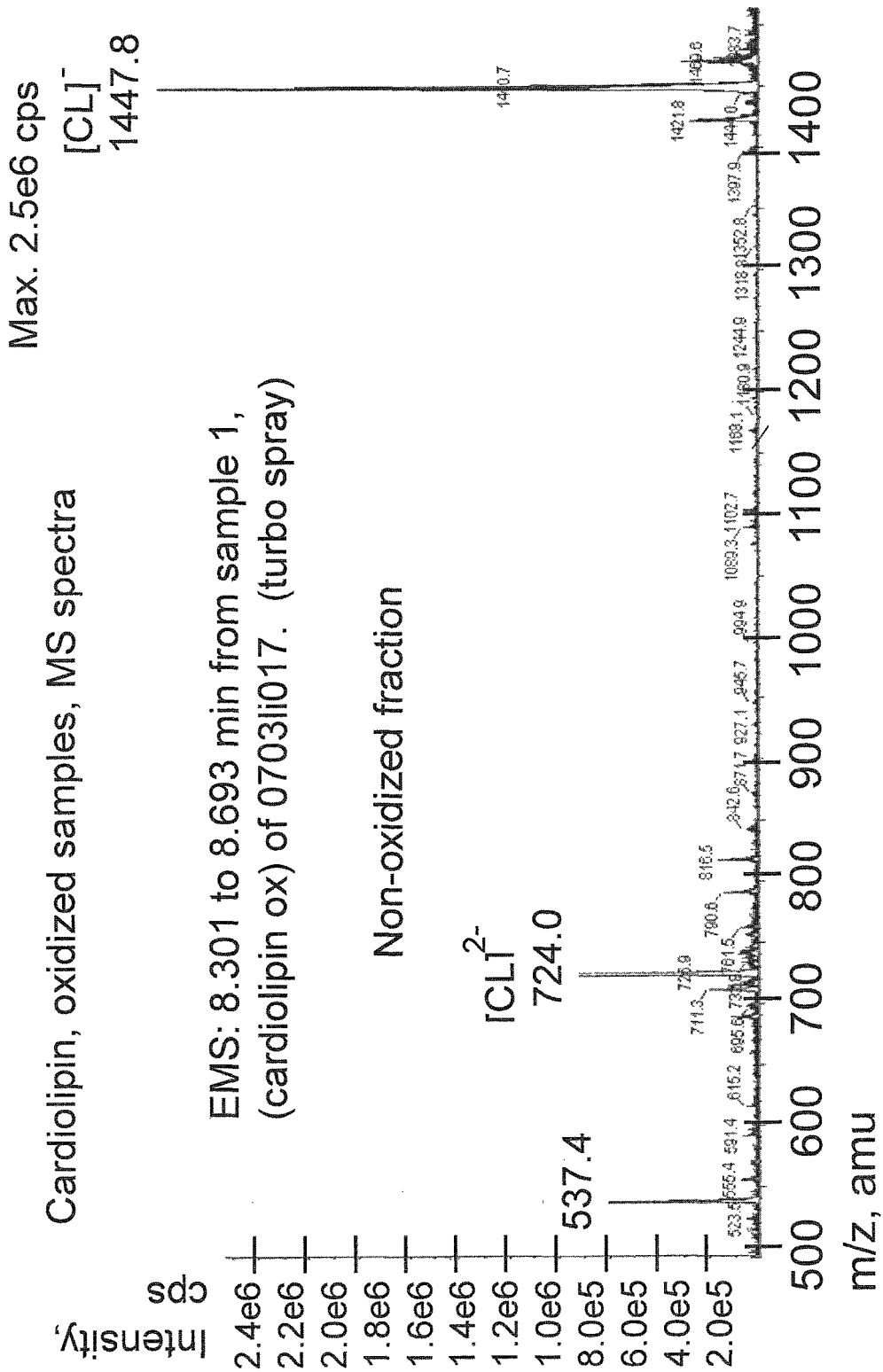

(60) Provisional application No. 61/138,966, filed on Dec. 19, 2008.

(51) Int. Cl.

| | |
|---|---|
| C07K 16/18 | (2006.01) |
| G01N 33/53 | (2006.01) |
| A61K 38/17 | (2006.01) |
| G01N 33/564 | (2006.01) |
| G01N 33/92 | (2006.01) |
| C07K 16/44 | (2006.01) |

(52) U.S. Cl.
CPC ... *G01N 2800/32* (2013.01); *G01N 2800/324* (2013.01); *G01N 2800/50* (2013.01)

(56) References Cited

U.S. PATENT DOCUMENTS

| | | | |
|---|---|---|---|
| 4,447,233 A | 5/1984 | Mayfield | |
| 4,486,194 A | 12/1984 | Ferrara | |
| 4,487,603 A | 12/1984 | Harris | |
| 4,596,556 A | 6/1986 | Morrow et al. | |
| 4,790,824 A | 12/1988 | Morrow et al. | |
| 4,941,880 A | 7/1990 | Burns | |
| 5,064,413 A | 11/1991 | McKinnon et al. | |
| 5,312,335 A | 5/1994 | McKinnon et al. | |
| 5,383,851 A | 1/1995 | McKinnon et al. | |
| 5,399,163 A | 3/1995 | Peterson et al. | |
| 2003/0152513 A1* | 8/2003 | Blankenberg ........ | A61K 51/087 424/1.49 |
| 2008/0044404 A1* | 2/2008 | Cederholm ........ | A61K 38/1709 424/130.1 |
| 2012/0014920 A1 | 1/2012 | Feng et al. | |

FOREIGN PATENT DOCUMENTS

| | | |
|---|---|---|
| WO | WO 2005/099744 | 10/2005 |
| WO | WO 2009/103977 | 8/2009 |
| WO | WO 2011/160845 | 12/2011 |

OTHER PUBLICATIONS

Post et al., (J Nucl Med. Oct. 2002;43(10):1359-65.*
European Office Action for EP 13 188 367.0-1408 dated Feb. 20, 2015.
M I Rodriguez-Garcia, et al., "Annexin V Autoantibodies in Rheumatoid Arthritis", 1996, pp. 895-900, vol. 55, Ann Rheum Dis.
C.P.M. Reutelingsperger, et al., "Annexin V, the Regulator of Phosphatidylserine-Catalyzed Inflammation and Coagulation during Apoptosis", 1997, pp. 527-532, vol. 53, CMLS Cellular and Molecular Life Sciences.
Pascale Chollet, MD, et al., "Annexin V-Coated Intraocular Lenses", 1996, pp. 818-824, vol. 22, J Cataract Refract Surg.
Thierry Dubois, et al., "High Levels of Antibodies to Annexins V and VI in Patients with Rheumatoid Arthritis", 1995, pp. 1230-1234, vol. 22, No. 7, The Journal of Rheumatology.
Robin L. Brey, MD, et al., "ß$_2$-Glycoprotein 1-Dependent Anticardiolipin Antibodies and Risk of Ischemic Stroke and Myocardial Infarction", 2001, pp. 1701-1706, vol. 32, Stroke.
Outi Vaarala, et al., "Anticardiolipin Response in Acute Infections", 1986, pp. 8-15, vol. 41, Clinical Immunology and Immunopathology.
Rulhua Wu, et al., "Antibodies Against Cardiolipin and Ocidatively Modified LDL in 50-Year-Old-Men Predict Myocardial Infarction", 1997, pp. 3159-3163, vol. 17, Arteriosclerosis, Thrombosis and Vascular Biology, doi:10.1161/01.ATV.17.11.3159.
Silva S. Pierangeli, et al., "Antiphospholipid Antibodies in an in vivo Thrombosis Model in Mice", 1994, pp. 247-251, vol. 3, Lupus.
Huiyong Yin, et al., "Free Radical Oxidation of Cardiolipin: Chemical Mechanisms, Detection and Implication in Apoptosis, Mitochondrial Dysfunction and Human Diseases", Jan. 1, 2012, pp. 1-16, Free Radical Research, XP007922100.
Basova LV et al: "Cardiolipin switch in mitochondria: shutting off the reduction of cytochrome c and turning on the peroxidase activity." *Biochemistry.* (2007) 46:3423-34.
Belikova NA et al: "Cardiolipin-specific peroxidase reactions of cytochrome C in mitochondria during irradiation-induced apoptosis." *Int J Radiat Oneal Biol Phvs.* (2007) 69: 176-86.
Cederholm A et al: "Decreased binding of annexin v to endothelial cells—a potential mechanism in atherothrombosis of patients with systemic lupus erythematosus." *Arteriosclerosis, Thrombosis, and Vascular Biology*, Lippincott Williams & Wilkins, US. (Jan. 1, 2005) 25: 1: 198-203.
Cederholm A et al: "Frostegard J. Annexin A5 in cardiovascular disease and systemic lupus erythematosus." Immunobioloar.(2005) 210:761-8.
Chauhan Asha et al: "Interaction of amyloid beta-protein with anionic phospholipids: Possible involvement of Lys28 and C-terminus aliphatic amino acids." *Neurochemical Research, Plenum Press, New York, US LNG* D01:10.1023/A:1007509608440. (Mar. 1, 2000) 25:3:423-429.
Chicco AJ et al: "Role of cardiolipin alterations in mitochondrial dysfunction and disease." *Am J Physiol Cell Physiol.* (2007) 292:C33-44.
Deguchi H et al: "Cardiolipin is a normal component of human plasma lipoproteins." *Proc Natl Acad Sci US A.* (2000) 97:1743-8.
Febbraio M et al: "Targeted disruption of the class B scavenger receptor CD36 protects against atherosclerotic lesion development in mice. J Clin Invest." (2000) 105: 1049-56.
Frostegard J et al: "Cytokine expression in advanced human atherosclerotic plaques: dominance of pro-inflammatory (Th1) and macrophage stimulating cytokines." *Atherosclerosis.* (1999) 145:33-43.
Frostegard J: "Atherosclerosis in patients with autoimmune disorders." *Arterioscler Thromb Vase Biol.* (2005) 25: 1776-85.
Frostegard Johan et al: "Lipid peroxidation is enhanced in patients with systemic lupus erythematosus and is associated with arterial and renal disease manifestations." *Arthritis & Rheumatism.* (Jan. 2005) 52: 1: 192-200.
Funk CD: "Leukotriene modifiers as potential therapeutics for cardiovascular disease." *Nat Rev Drug Discov.* (2005) 4:664-72.
Gonzalvez Fetal: "Cardiolipin: setting the beat of apoptosis." *Apoptosis.* (2007) 12:877-85.
Goodarzi K et al: "Leukotriene 84 and BL T1 control cytotoxic effector T cell recruitment to inflamed tissues." *Nat lmmunol.* (2003) 4:965-73.
Hamsten A et al: "Antibodies to cardiolipin in young survivors of myocardial infarction: an association with recurrent cardiovascular events." *Lancet.* (1986) 1 :113-6.
Han X et al: "Alterations in myocardial cardiolipin content and composition occur at the very earliest stages of diabetes: a shotgun lipidomics study." *Biochemistrv.* (2007) 46:6417-28.
Hansson GK: "Inflammation, atherosclerosis, and coronary artery disease." *N Engl J Med.* (2005) 352: 1685-95.
Horkko S et al: "Antiphospholipid antibodies are directed against epitopes of oxidized phospholipids. Recognition of cardiolipin by monoclonal antibodies to epitopes of oxidized low density lipoprotein." *The Journal of Clinical Investigation* Aug. 1, 1996. (Aug. 1, 1996) 98:3:815-825.
International Preliminary Report on Patentability for PCT /EP2009/ 009199, dated Jun. 19, 2011.
International Search Report for PCT/EP2009/009199, dated Oct. 4, 2010.
Ishii H et al: "Recombinant Annexin-2 inhibits the progress of diabetic nephropathy in a diabetic mouse model via recovery of hypercoagulability." *Thromb Haemost.* (2007) 97:124-8.
Martin W et al: "An overview of endosymbiotic models for the origins of eukaryotes, their ATP-producing organelles (mitochondria and hydrogenosomes), and their heterotrophic lifestyle." *Biol Chem.* (2001) 382:1521-39.
Moore KJ et al: "Scavenger receptors in atherosclerosis: beyond lipid uptake." *Arterioscler Thromb Vase Biol.* (2006) 26:1702-11.

(56) References Cited

OTHER PUBLICATIONS

Nakagawa Y: "Initiation of apoptotic signal by the peroxidation of cardiolipin of mitochondria." *Ann N Y Acad Sci.* (2004) 1011:177-84.
Pope S et al: "Oxidative stress and mitochondrial dysfunction in neurodegeneration; cardiolipin a critical target?" *Biochimica et Biophysica Acta.—Bioenergetics, Amsterdam, NL LNKD* 001: 10.1016/J.BBABI0.2008.03.011. (Jul. 1, 2008) 1777:7-8:794-799.
Pratico Domenico et al: "Circulating autoantibodies to oxidized cardiolipin correlate with isoprostane F2alpha-VI, levels and the extent of atherosclerosis in ApoE-deficient mice: Modulation by vitamin E." *Blood.* (Jan. 15, 2001) 97:2, 15:459-464.
Qiu H et al: "Expression of 5-lipoxygenase and leukotriene A4 hydrolase in human atherosclerotic lesions correlates with symptoms of plaque instability." *Proc Natl Acad Sci US A.* (2006) 103:8161-6.
Rand JH et al: "Antibody-mediated disruption of the annexin-V antithrombotic shield: a new mechanism for thrombosis in the antiphospholipid syndrome." *Thromb Haemost.* (1999) 82:649-55.
Sch Lame M: "Cardiolipin synthesis for the assembly of bacterial and mitochondrial membranes." *J Lipid Res.* (2008) 49:1607-20.
Schlame M et al: "Effect of cardiolipin oxidation on solid-phase immunoassay for antiphospholipid antibodies." *Thrombosis and Haemostasis, SchattauerGmbh, De; Us.* (Dec. 1, 2001) 86:6:1475-1482.
Schlame Met Al: "Deficiency of tetralinoleoyl-cardiolipin in Barth syndrome." *Ann Neurol.* (2002) 51 :634-7.
Schlame Met Al: "The biosynthesis and functional role of cardiolipin." *Prog Lipid Res.* 2000) 39:257-88.
Serezani CH et al: "Leukotrienes enhance the bactericidal activity of alveolar macrophages against Klebsiella pneumoniae through the activation of NADPH oxidase." *Blood.* (2005) 106:1067-75.
Sjoberg BG et al: "Low levels of IgM antibodies against phosphorylcholine—a potential risk marker for ischemic stroke in men", *Atherosclerosis.* (2008) 203: 528-532.
Sparagna GC et al: "Loss of cardiac tetralinoleoyl cardiolipin in human and experimental heart failure." *J Lipid Res.* (2007) 48:1559-70.
Thiagarajan P et al: "Inhibition of arterial thrombosis by recombinant annexin Vin a rabbit carotid artery injury model." *Circulation.* (1997) 96:2339-47.
Tuominen Anu et al: "A nature al antibody to oxidized cardiolipin binds to oxidized low-density lipoprotein, apoptotic cells, and atherosclerotic lesions." *Arteriosclerosis, Thrombosis, and Vascular Biology* Sep. 2006. (Sep. 2006) 26:9:2096-2102.
V Aarala 0 et al: "Crossreaction between antibodies to oxidised low-density lipoprotein and to cardiolipin in systemic lupus erythematosus." *Lancet.* (1993) 341 :923-5.
Vaarala Outi et al: "Anti-cardiolipin antibodies and risk of myocardial infarction in a prospective cohort of middle-aged men." *Circulation.* (1995) 91: 1 :23-27.
Wan Met Al: "Leukotriene 84 triggers release of the cathelicidin LL-37 from human neutrophils: novel lipid-peptide interactions in innate immune responses." *Faseb j.* (2007) 21 :2897-905.
Winyard PG et al: "Presence of foam cells containing oxidised low density lipoprotein in the synovial membrane from patients with rheumatoid arthritis." *Ann Rheum Dis.* (1993) 52:677-80.
Written Opinion of the International Searching Authority for PCT/EP2009/009199, dated Jun. 19, 2011.
Yokomizo T et al: "A G-protein-coupled receptor for leukotriene 84 that mediates chemotaxis." *Nature.* (1997) 387:620-4.
Yokomizo T et al: "A second leukotriene 8(4) receptor, BL T2. A new therapeutic target in inflammation and immunological disorders." *J Exp Med.* (2000) 192:421-32.
Zhou X et al: "LDL immunization induces T-cell-dependent antibody formation and protection against atherosclerosis." *Arteriosclerosis, Thrombosis, and VascularBioloav* Jan. 2001. (Jan. 2001) 21:1:108-114.
"Arthrex-ABPS Autologous Blood Processing System". Arthrex Vet Systems, München-Freiham, Germany, dated 2016.
"Osteoarthritis" —NHS Choices, accessed from http://www.nhs.uk/conditions/osteoarthritis/Pages/Introduction.aspx on Aug. 4, 2016.
"Osteoarthritis" —NHS Choices, accessed from http://www.nhs.uk/conditions/osteoarthritis/Pages/treatment.aspx on Aug. 4, 2016.
Bhadra et al. (2002). Pegnology: a review of PEG-ylated systems. Pharmazie. 57(1):5-29.
Bozic et al. (1997). Influence of degraded phosphatidylserine on binding of antiphospholipid antibodies. Int Arch Allergy Immunol. 112(1):19-26.
Charlier et al. (2016). Insights on Molecular Mechanisms of Chondrocytes Death in Osteoarthritis. Int J Mol Sci. 17(12):2146.
de Rezende & de Campos (2013). Is osteoarthritis a mechanical or inflammatory disease? Rev Bras Ortop. 48(6):471-4.
de Souza (2016). Osteoarthritis in horses—Part 1: relationship between clinical and radiographic examination for the diagnosis. Braz Arch Biol Technol. 59:e16150024.
Ea et al. (2008). Annexin 5 overexpression increased articular chondrocyte apoptosis induced by basic calcium phosphate crystals. Ann Rheum Dis. 67(11):1617-25. Epub Jan. 24, 2008.
Ewing et al. (2011). Annexin A5 therapy attenuates vascular inflammation and remodeling and improves endothelial function in mice. Arterioscler Thromb Vasc Biol. 31(1):95-101.
Experimental report in respect of European Patent Application No. 09796630.3, dated Mar. 31, 2017.
Frostegård (2010). Low level natural antibodies against phosphorylcholine: a novel risk marker and potential mechanism in atherosclerosis and cardiovascular disease. Clin Immunol. 134(1):47-54. Epub Sep. 11, 2009.
Harris et al. (2001). Pegylation: a novel process for modifying pharmacokinetics. Clin Pharmacokinet. 40(7):539-51.
Hiligsmann & Reginster (2013). The economic weight of osteoarthritis in Europe. Medicographia. 35(2):197-202.
House and Morton. "Interleukin-1 Receptor Antagonist Protein (IRAP®) Therapy for Equine Osteoarthritis". College of Veterinary Medicine, University of Florida, Gainesville, FL, accessed from http://extension.vetmed.ufl.edu/files/2011/10/IRAPFinal.pdf, dated 2011.
Kim & Kirsch (2008). Collagen/annexin V interactions regulate chondrocyte mineralization. J Biol Chem. 283(16):10310-7. Epub Feb. 14, 2008.
Kirsch et al. (2000). Activation of annexin II and V expression, terminal differentiation, mineralization and apoptosis in human osteoarthritic cartilage. Osteoarthritis Cartilage. 8(4):294-302.
Komori (2016). Cell Death in Chondrocytes, Osteoblasts, and Osteocytes. Int J Mol Sci. 17(12):2045.
Kozlowski & Harris (2001). Improvements in protein PEGylation: pegylated interferons for treatment of hepatitis C. J Control Release. 72(1-3):217-24.
Kozlowski et al. (2001). Development of pegylated interferons for the treatment of chronic hepatitis C. BioDrugs. 15(7):419-29.
Lee et al. (2002). Annexin 5 and apolipoprotein E2 protect against Alzheimer's amyloid-beta-peptide cytotoxicity by competitive inhibition at a common phosphatidylserine interaction site. Peptides. 23(7):1249-63.
Lorberboym et al. (2009). The use of 99mTc-recombinant human annexin V imaging for differential diagnosis of aseptic loosening and low-grade infection in hip and knee prostheses. J Nucl Med. 50(4):534-7. Epub Mar. 16, 2009.
Luong et al. (2001). Seasonal distribution of antiphospholipid antibodies. Stroke. 32(8):1707-11.
Mabey & Honsawek (2015). Cytokines as biochemical markers for knee osteoarthritis. World J Orthop. 6(1):95-105.
McCoy (2015). Animal models of osteoarthritis: comparisons and key considerations. Vet Path. 52(5):803-18.
McIlwraith et al. (2012). The horse as a model of naturally occurring osteoarthritis. Bone Joint Res. 1(11):297-309.
Munoz et al. (2007). The role of annexin A5 in the modulation of the immune response against dying and dead cells. Curr Med Chem. 14(3):271-7.
Pierangeli et al. (1994). Effect of human IgG antiphospholipid antibodies on an in vivo thrombosis model in mice. Thromb Haemost. 71(5):670-4.

(56) References Cited

OTHER PUBLICATIONS

Reddy (2000). Controlled-release, pegylation, liposomal formulations: new mechanisms in the delivery of injectable drugs. Ann Pharmacother. 34(7-8):915-23.

Roberts et al. (2002). Chemistry for peptide and protein PEGylation. Adv Drug Deliv Rev. 54(4):459-76.

Ross et al. (2012). Evaluation of the inflammatory response in experimentally induced synovitis in the horse: a comparison of recombinant equine interleukin 1 beta and lipopolysaccharide. Osteoarthritis Cartilage. 20(12):1583-90. Epub Aug. 21, 2012.

Stegnar et al. (1991). Prevalence of antiphospholipid antibodies in deep vein thrombosis and their relationship to blood coagulation and fibrinolysis. Thromb Res. 63(4):433-43.

Tuhrim et al. (1999). Antiphosphatidyl serine antibodies are independently associated with ischemic stroke. Neurology. 53(7):1523-7.

Vay et al. (2006). Anti-phospholipid antibodies associated with alcoholic liver disease target oxidized phosphatidylserine on apoptotic cell plasma membranes. J Hepatol. 44(1):183-9. Epub Jul. 11, 2005.

Vermes et al. (1995). A novel assay for apoptosis. Flow cytometric detection of phosphatidylserine expression on early apoptotic cells using fluorescein labelled Annexin V. J Immunol Methods. 184(1):39-51.

Veronese (2001). Peptide and protein PEGylation: a review of problems and solutions. Biomaterials. 22(5):405-17.

Von Landenberg et al. (2003). The combination of different antiphospholipid antibody subgroups in the sera of patients with autoimmune diseases is a strong predictor for thrombosis. A retrospective study from a single center. Immunobiology. 207(1):65-71.

Wan (2010). Studies on leukotriene B4 and alarmins in inflammatory responses. Ph.D. Thesis, Department of Medical Biochemistry and Biophysics, Karolinska Institutet, Stockholm, Sweden. Jan. 29, 2010.

Wan et al. (2014). Oxidized but not native cardiolipin has pro-inflammatory effects, which are inhibited by Annexin A5. Atherosclerosis. 235(2):592-8.

\* cited by examiner

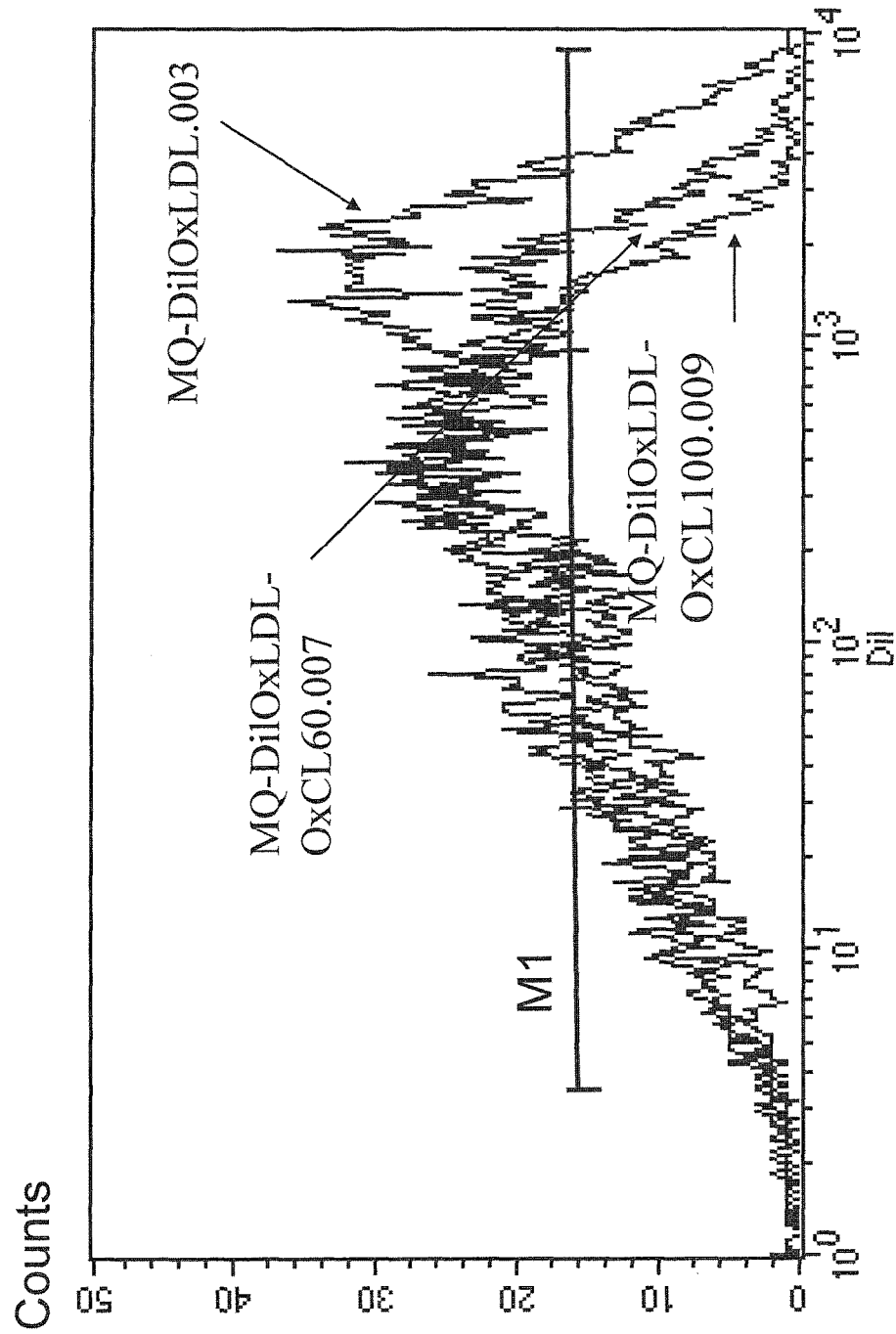

OXIDIZED CARDIOLIPIN AS A PRO-INFLAMMATORY FACTOR

CROSS REFERENCE TO RELATED APPLICATIONS

This is a divisional of application Ser. No. 13/140,906, filed Jun. 20, 2011 (which is hereby incorporated by reference), which is a § 371 National Stage of International Application No. PCT/EP2009/009199 filed Dec. 21, 2009 (which is hereby incorporated by reference), which claims benefit of U.S. Provisional Application No. 61/138,966, filed Dec. 19, 2008 (which is hereby incorporated by reference).

FIELD OF THE INVENTION

The present invention relates to methods of monitoring, determining, or influencing the level of antibodies against oxidized cardiolipin (anti-oxCL) in a bodily fluid from a mammal. It is shown that low level of anti-oxCL is correlated with a higher risk of developing cardiovascular disease, auto-immune diseases or inflammatory conditions. Thus, the invention relates also to a kit and the use of anti-oxCL as a diagnostic marker for determining the risk of developing a cardiovascular disease, an auto-immune disease or an inflammatory condition. Further, the invention relates to the use of agents for activation immunotherapy and for the manufacture of a medicament for treating, preventing, and/or reducing the risk of developing a cardiovascular disease, an auto-immune disease or an inflammatory condition.

BACKGROUND OF THE INVENTION

Auto-immune disease and inflammatory conditions are major health problems in the Western world and increasingly in developing countries. These diseases include Rheumatic conditions like Rheumatoid arthritis and Systemic lupus erythematosus (example of autoimmune diseases), the latter often described as a prototypic autoimmune disease, and in text books more than 80 autoimmune rheumatic diseases are described, cf. e.g. Harrison's Principles of Internal Medicine, 17th Edition, which hereby is incorporated by reference. In addition, conditions like inflammatory bowel disease, asthma and diabetes type 1 are examples of auto-immune conditions.

Interestingly and importantly, atherosclerosis and its consequences stroke, myocardial infarction, acute coronary syndromes and heart failure during recent years have been demonstrated to be inflammatory conditions, with activated inflammatory and immune competent cells typically present in the atherosclerotic plaques.

Further, also dementia including Alzheimer's disease, is characterized by chronic inflammation, which has also been demonstrated for osteoarthritis.

Treatment modalities against inflammation in these diseases vary, but in general have not been successful, with Rheumatoid arthrititis as a possible exception and there is a clear need of new types of treatment. Further, prediction by use of biomarkers is not optimal, and in many cases there is a great need of new types of treatment.

Cardiolipin (CL) is a dimeric phospholipid which is known to be present in eucarytic cells, bacteria and Archaebacteria but its functional role is only partly known, (Schlame M., 2008)[1]. It is more prevalent in cells with high metabolic activity, like heart and skeletal muscle, and especially in mitochondrial membranes. The presence of CL in mitochondria and bacteria is interesting from an evolutionary point of view since mitochondria are likely to have a bacterial origin, (Martin. W et al, 2001)[2]. Also lipoproteins including low density lipoprotein (LDL) contain CL in contrast to what has previously has been thought, and two thirds of CL are present in low density lipoprotein (LDL), (Deguchi et al, 2000)[3].

CL has a unique dimeric structure, highly enriched in linoleic acid groups susceptible to oxidation (Schlame, M. et al, 2000, and Chicco, A J et al, 2007)[4,5]. It has been suggested to play a role in generation of an electrochemical potential for substrate transport and ATP synthesis both in bacteria and mitochondria, (Belikova, N A. et al, 2007 and Bosova L V, el at, 2007)[6,7]. CL that has undergone oxidation (oxCL) promotes delocalization and release of cytochrome c, predisposing to its release from mitochondria and the activation of the cell death programmes, (Chicco, A J. Et al, 2007, Gonzalzez, F. et al, 2007 and Nakagawa, Y., 2004)[5,8,9].

Antibodies against CL (aCL) cause both venous and arterial thrombosis, and are known to be of major importance in rheumatic diseases, especially lupus erythematosus SLE by promoting cardiovascular disease and venous thrombosis, (Frostegard, J., 2005)[10] and very high levels of aCL are also linked to cardiovascular disease CVD in the general population, (Hamsten, A. et al, 1986)[11].

Annexin A5 is a member of the Annexin superfamily and has anti-thrombotic properties due to interaction with phospholipids, especially phosphatidylserine, and thus the coagulation cascade. It has recently been demonstrated that aCL decrease binding of Annexin A5 to endothelial cells and it has been suggested that Annexin A5 could have anti-atherothrombotic properties in general, (Cederholm, A. et al, 2005)[12]. Further, aCL cross reacts with oxidized low density lipoprotein (oxLDL), (Vaarala, O. et al, 1993)[13]. Since oxLDL is likely to be of major importance in atherosclerosis and is present in large amounts in the atherosclerotic lesions, (Hansson, G K., 2005)[14], the association with aCL could have clinical implications.

SUMMARY OF THE INVENTION

Cardiolipin (CL) is a phospholipid with an unusual dimeric phospholipids structure, present in mitochondria and bacteria, but also in lipoproteins. The properties of oxidized CL (oxCL) and inhibitory effects of Annexin A5, an antithrombotic agent interfering with phospholipids, are determined.

It has been found that oxCL in contrast to CL has pro-inflammatory properties of relevance in atherogenesis and also rupture of atherosclerotic plaques. These effects could be inhibited by Annexin A5. The implications of these findings are discussed.

The surprising characteristics of oxCL are confirmed by the fact that low concentrations of antibodies to mammal oxCl are an effective indicator of a cardiovascular disease, an auto-immune disease or inflammatory condition. It is within this present invention found that antibodies to this particular antigen does not develop sufficiently in patients before the clinical onset of cardiovascular disease, an auto-immune disease or inflammatory condition and presently it is a preferred hypothesis that an insufficiently developed natural immunity against oxCL represents an underlying mechanism for development of such diseases.

In connection with the present invention mammals means all known mammals and in particular mice, rats, rabbits, dogs, cats, cattle, horses and human.

In connection with the present invention bodily fluid means any natural bodily fluid or secretion of fluid including but not limited to plasma, serum, blood, urine, or saliva.

In connection with the present invention cardiovascular disease, an auto-immune disease or inflammatory condition means any of—including but not limited to—the following diseases: cardiovascular disease (CVD), diabetes II, Alzheimer's disease, dementia in general, rheumatic diseases, atherosclerosis, high blood pressure, acute and/or chronic inflammatory conditions, myocardial infarction, acute coronary syndrome, stroke, transient ischemic attack (TIA), claudiction, angina, type I diabetes, rheumatoid arthritis, psoriasis, psoriatic arthritis, ankylosing spondylitis, Reiter's Syndrome, systemic lupus erythematosus, dermatomyositis, Sjogren's syndrome, lupus erythematosus, multiple sclerosis, myasthenia gravis, asthma, encephalitis, inflammatory bowel disease, chronic obstructive pulmonart disease (COPD), arthritis including osteoarthritis, idiopathic inflammatory myopathies (IIM), dermatomyositis (DM), polymyositis (PM), inclusion body myositis, an allergic disorder and/or osteoarthritis in a mammal.

In connection with the present invention antibodies against oxCl (anti-oxCL) may be determined using any of the methods and techniques conventional in the art for such determination. Conveniently, such a method may comprise an immunoassay e.g. ELISA, EIA, immunofluorescence, Western blot, immunodiffusion, immunoelectrophoresis, immuno precipitation and Magnetic immunoassay. Conveniently, the components needed to perform the immunoassay will be supplied in a kit form.

In connection with the present invention a medicament may be intended for parenteral and mucosal administration and may be formulated with excipients normally employed for such formulations. The medicament may be administered in a way so as to be compatible with the dosage formulation and in such amount as will be therapeutically effective and immunogenic.

In connection with the present invention vaccine means any agent that is suitable for increasing the anti-oxCL response, in particular oxCL or bioactive components and/or parts thereof optionally in combination with any suitable adjuvants.

In connection with the present invention monoclonal or polyclonal antibodies of isotype IgA, IgD, IgE, IgG, IgM, raised against oxCL or bioactive components and/or parts/fragments thereof refers to any monoclonal or polyclonal antibody produced by immunisation of a suitable mammal, including but not limited to mouse, rabbit, goat, sheep, or horse.

Also provided is method of treating, preventing or reducing the risk of developing a cardiovascular disease, an auto-immune disease or inflammatory condition in an mammal wherein said cardiovascular disease, an auto-immune disease or inflammatory condition is/are selected from the group comprising cardiovascular disease, diabetes II, Alzheimer's disease, dementia in general, rheumatic diseases, atherosclerosis, high blood pressure, acute and/or chronic inflammatory conditions, myocardial infarction, acute coronary syndrome, stroke, TIA, claudiction, angina, type I diabetes, rheumatoid arthritis, psoriasis, psoriatic arthritis, ankylosing spondylitis, Reiter's Syndrome, systemic lupus erythematosus, dermatomyositis, Sjogren's syndrome, lupus erythematosus, multiple sclerosis, myasthenia gravis, asthma, encephalitis, inflammatory bowel disease, chronic obstructive pulmonary disease (COPD), arthritis, idiopathic inflammatory myopathies (HM), dermatomyositis (DM), polymyositis (PM), inclusion body myositis, an allergic disorder and/or osteoarthritis, comprising administering to a mammal in need thereof a therapeutically effective amount of an agent that inhibits the activity of oxCL. The agent that inhibits the activity of oxCL may be selected from the group consisting of Annexin A5, or a monoclonal or polyclonal antibody of isotype IgA, IgD, IgE, IgG, IgM, raised against oxCL or bioactive components and/or parts/fragments thereof, optionally in combination with any suitable adjuvants.

DETAILED DESCRIPTION OF THE INVENTION

The major underlying cause of CVD is atherosclerosis, which is nowadays regarded as an inflammatory condition. However, it is mainly when atherosclerotic plaques rupture or are otherwise damaged that CVD occurs, typically at sites with an ongoing inflammatory process, (Hansson, G K., 2005 and Frostegard, J: et al 1999)[14,15]. It is therefore of major importance to identify underlying proinflammatory factors in atherogenesis and CVD.

It has been found that oxidized CL, in contrast to native CL, has pro-inflammatory properties. The oxidation of native CL frok bovine heart was confirmed with mass spectrophotometer.

OxCL but not CL induced endothelial cells to express ICAM-1, intracellular adhesion molecule 1, and VCAM-1, vascular cell adhesion molecule 1. Adhesion molecules play an important role to recruit monocytes into interstitial in the artery, which is likely to be an early step in atherogenesis and inflammatory process for development of atherosclerosis.

Further, it is found and demonstrated that oxCL has the capacity to induce interleukin 6, IL-6, production, but not CL. Several clinical studies have implicated three well-known markers of inflammation, C-reactive protein (CRP), fibrinogen (Fb) and IL-6, as CVD risk factors, and IL-6 has been identified as an independent risk factor for coronary artery disease (CAD).

Furthermore, it is in this present invention reported that oxCL but not CL could inhibit Leucotrine B4, LTB4, production in both neutrophils and macrophages. It is also found that OxCL but not CL can provoke interacellular calcium mobilization which is an initiation signal for LTB4 production and also in general a sign of cell activation. Leukotrines are short-lived lipid mediators that have potent pro-inflammatory biological activities. Leukotriene B4 (LTB4) is one of the most potent chemotactic agent for other inflammatory cells and is biosynthesized from arachidonic acid by the sequential action of 5-lipoxygenase (5-LO) and Leucotrine A4, LTA4, hydrolase, mainly in cells of myeloid lineage, such as neutrophil and macrophage, (Funk, C D., 2005)[16]. Two G-protein coupled LTB4 receptors have been identified, BLT1 and BLT2, with high and low affinity for LTB4, respectively, (Yokomizo, T. et al, 1997 and Yokomizo, T. et al, 2000)[17,18]. LTB4 is known to exert broad pro-inflammatory effects, and evidence is accumulating regarding the antimicrobial functions of LTB4, (Serezani, C H. Et al, 2005 and Wan, M. et al, 2007)[19,20]. Furthermore, the LTB4-BLT1 pathway was found to be important for linking early immune responses and the multiple classes of effector cells associated with acquired immunity, (Goodarzi, K. et al, 2003)[21]. LTB4 may play an important role in atherosclerosis and CVD since mRNA levels for the three key proteins are significantly increased in human atherosclerotic plaque, and more pronounced in patients with ongoing CVD, (Qui, H. et al, 2006)[22].

Thus, by inducing LTB4, oxCL could therefore play a role in initiating plaque rupture and CVD. Another finding herein is that oxCL but not CL (or reduced CL) inhibits uptake of oxLDL in macrophages.

OxLDL is taken up through specific scavenger receptors, which are not down-regulated when exposed to increasing amounts of oxLDL (as opposed to the uptake of LDL), (Hansson, G K., 2005)[14]. Inhibition of the scavenger function is generally believed to be atheroprotective, preventing foam cell formation in the vascular wall which is a key process in development of atherosclerosis. In line with this, mice defective in scavenger receptor function develop less atherosclerosis as compared to control mice, (Febraio, M. et al, 2000)[23]. It should be noted, however, that recent research indicates that different scavenger receptors may play different roles and the role of scavenger receptors may vary depending on disease stage and type, (Moore, K J. et al, 2006)[24].

If oxCL is predominantly exposed on oxLDL, binding and uptake of oxLDL could through oxCL could promote atherogenesis. On the other hand, if oxCL is present mainly on other compounds, e.g. apoptotic cells, other proteins, or even bacteria, it is not clear how this would influence foam cell development, which in principle could be decreased. However, since apoptotic cells are known not to have any pronounced proinflammatory effects, this would suggest at least that oxCL is not an important factor exposed during apoptosis. Further research is needed to clarify which parts of oxLDL play the largest role in foam cell formation.

It has recently been demonstrated that Annexin A5 is abundant in atherosclerotic lesions and that aCL can interfere with its binding to endothelial cells, promoting CVD in SLE, (Cederholm, A. et al, 2005)[12]. Rand et al have demonstrated that Annexin A5 can form a crystalline shield over cell surfaces, which could have a protective function. However, this can be disrupted by aCL, causing the antiphospholipid antibody syndrome, characterized by arterial and venous thrombosis and also miscarriage, (Rand, J H. Et al, 1999)[25]. Annexin A5, ANXA5, has recently been implicated in CVD in general also as indicated by its function as a potent antiatherothrombotic agent in a rabbit model of arterial thrombosis, by interfering with tissue factor expression and by recovery of hypercoagulability, (Cederholm, A. et al, 2005, Thiagarajan, P. et al, 1997 and Ishii, H. et al, 2007)[26-28].

In connection with the present invention novel anti-inflammatory properties of Annexin A5, with potential interest in atherosclerosis and CVD are reported. Annexin A5 inhibited the proinflammatory effects of oxCL, including induction of adhesion molecules, IL-6 The mechanism could be that Annexin A5 binds to phosphatidylserine (PS) of endothelial cells, PS being a prothrombotic factor. It is also demonstrated that Annexin A5 can bind to OxCL but not CL, though the exact mechanisms are not clear. Annexin A5 can thus in principle prevent these oxCL-induced effects by interacting with oxCL, though the exact mechanisms remain to be shown. Compatible with this is the unusual properties of Annexin A5, enabling it to form crystalline layers, which by themselves could be of anti-inflammatory, inhibiting pro-inflammatory effects of oxCL by a mechanistic barrier.

CL is synthesized in cells de novo through the action of cardiolipin synthases which is most active in high-metabolic tissue (where CL itself is most abundant). In mitochondria, CL modification and remodelling occurs including substantial changes in the acyl composition[1]. Accumulating evidence now also suggests that remodeling defects of CL could play a role in physiology and also pathology such as in diabetes, heart failure and Barth's syndrome, (Han, X. et al, 2007, Sparagna, G C. Et al, 2007 and Schlame, M, 2002)[29-31]. In an interesting report it was demonstrated that CL is quickly oxidized when coated on ELISA-plates for determination of aCL and many aCL in fact recognize oxidized CL (oxCL), (Horkko, S. et al, 1996)[32]. oxCL being an antigen for aCL could thus contribute to the antiphospholipid antibody syndrome, (Horkko, S. et al, 1996)[32]. The nature of these antibodies is still debated, almost three decades after their discovery, and it is likely that some aCL recognize plasma protein co-factors binding to CL, but that others recognize the phospholipid moiety, (Frostegard, J., 2005)[10].

Based on the findings herein, it is hypothesized that CL also could contribute to human chronic inflammatory disease in general and CVD in particular, by its proinflammatory effects. CL binds easily to proteins, and it is possible that such complexes can become proinflammatory e.g. if exposed to the hypoxic and/or prooxidant environment in atherosclerotic plaques, but in principle also in other chronic inflammatory conditions like rheumatoid arthritis (RA) and SLE.

Interestingly, oxLDL and foam cells are present in rheumatoid arthritis, RA-synovia, (Winyard, P G. et al, 1993)[33], and oxLDL is raised and associated with disease activity in RA (unpublished observation). In systemic lupus erythematosus (SLE), the risk of CVD is very high due to a combination of traditional and non-traditional risk factors, (Frostegard, J., 2005)[10]. Both aCL and oxLDL are important examples of non-traditional risk factors. In addition to being raised in SLE per se, oxLDL is CVD in SLE, (Frostegard, J., 2005 and Frostegard, J. et al, 2005)[10,34]. Since CL is easily oxidized, it could play a role in these chronic inflammatory conditions.

It has recently been demonstrated that low levels of natural antibodies against phosphorylcholine (anti-PC), another exposed antigen in oxLDL, are risk factors for development of CVD in men, (Sjoberg, B G, 2008)[35]. phosphorycholine, oxCL belongs to a novel class of pathogen-associated molecular patterns (PAMPs) and natural antibodies against oxCL bind oxLDL, (Tuominen, A, 200)[36]. Thus, it is not known if there are common patterns of recognition in oxCL and PC, but the possibility that natural antibodies against oxCL like anti-PC, are risk factors for CVD at low levels deserves further study.

Taken together, the findings of the present invention indicate that oxCL can be a novel pro-inflammatory factor, causing or promoting plaque rupture in CVD and potentially also playing a role in other chronic inflammatory conditions including RA and SLE. Further, based on its capacity to inhibit oxCL-effects, it can be hypothesized that Annexin A5 also known as ANXA5, could be developed into a therapeutic agent in atherothrombosis and plaque rupture and also in other inflammatory conditions where oxCL plays a role.

Immunoassays

Detection of antibodies is a common form of medical diagnostics. For example, in different biochemical assays for disease diagnosis, a titer of antibodies indicative for a particular disease is estimated from the blood and if those antibodies are not present, the person does not have the disease in question.

Several immunodiagnostic methods based on detection of complex antigen-antibody are used to diagnose infectious diseases, for example ELISA, immunofluorescence, Western blot, immunodiffusion, immunoelectrophoresis, and Magnetic immunoassay. Targeted monoclonal antibody therapy has been used to treat diseases such as rheumatoid arthritis, multiple sclerosis, psoriasis, and many forms of cancer including non-Hodgkin's lymphoma, colorectal cancer, head and neck cancer and breast cancer.

An immunoassay is a test that measures the concentration of a substance in a bodily fluid, using the reaction of an antibody or antibodies to its antigen. Both polyclonal and monoclonal antibodies can be used. Monoclonal antibodies usually bind only to one site of a particular molecule, and therefore provide a more specific and accurate test. Both the presence of antigen or antibodies can be measured.

In many applications, the response of the bodily fluid being measured is compared to standards of a known concentration. This can be done through the plotting of a standard curve on a graph, the position of the curve at response of the unknown is then examined, and so the quantity of the unknown can be determined.

The most common method used for detecting the quantity of antibody or antigen is to label either the antigen or antibody. The label may consist of an enzyme (enzyme immunoassay (EIA, also called Enzyme-linked immunosorbant assay or ELISA), colloidal gold (lateral flow assays), radioisotopes such as I-125 Radioimmunoassay (RIA), magnetic labels (magnetic immunoassay—MIA) or fluorescence. Other techniques include agglutination, nephelometry, turbidimetry and Western Blot.

Immunoassays are normally divided into those that involve labelled reagents and those which involve non-labelled reagents. Those which involve labelled reagents can be subdivided into homogenous and heterogeneous immunoassays. Heterogeneous immunoassays can furthermore be competitive or non-competitive. In simple terms, in ELISA or EIA an antigen is affixed to a surface, and then an antibody is washed over the surface so that it can bind to the antigen. This antibody is then linked to an enzyme (e.g. through binding with an additional antibody), and in the final step a substance is added that the enzyme can convert to some detectable signal.

ELISA

Thus, any form of ELISA (it being direct ELISA, indirect ELISA, sandwich ELISA, competitive ELISA or reverse ELISA) can be performed to evaluate either the presence of antigen or the presence of antibody in a sample, and is consequently a useful tool for determining serum antibody concentrations.

The ELISA, or the enzyme immunoassay (EIA), has a high sensitivity. Thus, in an ELISA of relevance for the present invention, a sample of bodily fluid, e.g. a person's serum, can e.g. be diluted 400-fold and applied to a plate to which oxCL is attached. If antibodies to oxCL are present in the serum, they may bind to oxCL. The plate can then be washed to remove all other components of the serum. A specially prepared "secondary antibody"—an antibody that binds to the oxCL/anti-oxCL complex—can then be applied to the plate, followed by another wash. If this secondary antibody is chemically linked in advance to an enzyme, the plate will contain enzyme in proportion to the amount of secondary antibody bound to the plate. A substrate for the enzyme can then be applied, and catalysis by the enzyme leads to a change in color or fluorescence. ELISA results can then be reported as a number, which can subsequently be compared to the relevant "cut-off" point between a positive and negative result.

A cut-off point may be determined by comparing it with a known standard. This can be determined by applying a sample of known oxCL concentration to a surface and fixing it to the surface to render it immobile. Samples of known oxCL concentrations can then be used to generate a standard curve.

Activation Immuno-therapies

Immunotherapy is normally defined within medicine as "Treatment of disease by inducing, enhancing, or suppressing an immune response".

Passive immunity can be achieved through the transfer of ready-made antibodies into the affected individual. Immunotherapies designed to elicit or amplify an immune response are normally termed Activation Immunotherapies.

Immunotherapies designed to reduce, suppress or more appropriately direct an existing immune response, as in cases of autoimmunity or allergy, are normally termed Suppression Immunotherapies. The active agents of immunotherapy are collectively called immunomodulators.

Cut-off Value

The average level of anti-oxCL in mammals depends on the type of bodily fluid sample, the specific species, and may vary between the different population groups.

A cutoff value may be chosen so that concentrations of anti-oxCL lower than said cutoff value is associated with an increased risk of developing a cardiovascular disease, an auto-immune disease or inflammatory condition.

Thus, a suitable cut-off value for having a higher risk of developing a cardiovascular disease, an autoimmune disease and/or an inflammatory condition may be chosen to be 95%, 90%, 85%, 80%, 75%, 65%, 60%, 55%, 50%, 45%, 40%, 35%, 30%, 25% or even less, of the average levels of anti-oxCL usually present in the population, preferably less than 75%, more preferably less than 50% or even more preferably less than 33% or 25% of the average levels of anti-oxCL found in the given population.

A cutoff value may be chosen so that concentrations of anti-oxCL higher than said cutoff value is not associated with an increased risk of developing a cardiovascular disease, an auto-immune disease or inflammatory condition.

Thus, a suitable cut-off value for having a low risk of developing a cardiovascular disease, an autoimmune disease and/or an inflammatory condition may be chosen to be 30%, 40%, 50%, 60%, 70%, 76%, 78%, 80%, 82%, 84%, 86%, 88%, 90%, 92%, 94%, 96%, 98% of the average levels of anti-oxCL usually present in the population, preferably more than 30%, more preferable more than 50%, even more preferably more than 76% of the average levels of anti-oxCL found in the given population.

Embodiments of the Invention

In one embodiment the invention relates to a method for monitoring or determining the level of oxCL-antibodies (anti-oxCL) in a bodily fluid from a mammal.

Thus, in a particular embodiment of the invention it relates to an immunoassay making use of oxCL or parts thereof and a marker of antibody-origin for binding to anti-oxCUoxCL-complexes comprising a means for acquiring a quantity of the bodily fluid, a media having affixed thereto a capture antibody capable of complexing with anti-oxCL, and an assay for the detection of a complex of the capture antibody and the anti-oxCL. The immunoassay may preferably be ELISA, most preferably sandwich ELISA.

In a further embodiment the invention relates to the use of anti-oxCL in diagnostic in vitro methods as a diagnostic marker of mammal diseases wherein the level of anti-oxCL in a sample of bodily fluid from said mammal is used in the diagnosis of the risk of said mammal developing a cardiovascular disease, an auto-immune disease or inflammatory condition.

In a further embodiment the invention relates to a kit for detecting the presence of anti-oxCL in a bodily fluid said kit comprising a means for acquiring a quantity of the bodily fluid, a media having affixed thereto a capture antibody capable of complexing with anti-oxCL, and an assay for the detection of a complex of the capture antibody and the anti-oxCL.

In a further embodiment the invention relates to the use of an agent that inhibits the activity of oxCL for the manufacture of a medicament for treating, preventing and/or reducing the risk of developing a cardiovascular disease, an auto-immune disease or inflammatory condition in a mammal wherein the agent that inhibits the activity of oxCL is selected from the group consisting of Annexin A5, or a monoclonal or polyclonal antibody of isotype IgA, IgD, IgE, IgG, IgM, raised against oxCL or bioactive components and/or parts/fragments thereof.

In a further embodiment the invention relates to the use of oxCL or parts thereof for the manufacture of a medicament for use in activation immunotherapy in the treatment, prevention and/or reduction of the risk of developing a cardiovascular disease, an auto-immune disease or inflammatory condition in a mammal.

In a further embodiment the invention relates to a method of treating, preventing or reducing the risk of developing a cardiovascular disease, an auto-immune disease or inflammatory condition in an mammal wherein the agent that inhibits the activity of oxCL is selected from the group consisting of Annexin A5, or a monoclonal or polyclonal antibody of isotype IgA, IgD, IgE, IgG, IgM, raised against oxCL or bioactive components and/or parts/fragments thereof.

oxCL is a novel pro-inflammatory factor which plays a role in CVD and in inflammatory conditions and autoimmune diseases. Annexin A5 inhibits the effects of oxCL and could be developed into a therapeutic agent in atherothrombosis and plaque rupture and also in other inflammatory and autoimmune conditions where oxCL plays a role.

Experimental

The materials and methods and examples disclosed below are provided only for the purpose of illustrating the present invention and should not be considered as any limitation of the scope as outlined in the appended claims.

Materials and Methods

Chemical Treatments of Cardiolipin

Cardiolipin from bovine heart was purchased as ethanol solution from Sigma (Sigma product C 1649) and was stored at −20° C. Hydro heart cardiolipin (reduced CL) was purchased from Avanti Polar Lipids, Inc. To generate saturated molecular species, cardiolipin was oxidized in aqueous solutions containing 1.5 mmol/L tert-butylhydroperoxide and $CuSO_4$ in concentrations ranging 20 umol/L. Both cardiolipin and coppor treated cardiolipin were measured with MS-spectrophotometer, and it was confirmed to have been oxidized by copper and tert-butylhydroperoxide.

Endothelial Cells Culture and Adhesion Molecular

Pooled human umbilical vascular endothelial cells (HU-VECs) at passage 2 were purchased from Cascade Biologics, Inc (Portland, Ore). Cultures were maintained in EGM™ phenol red-free medium (Clonetics, San Diego, Calif.), containing 2% of fetal bovine serum and supplements, at 37° C. under humidified 5% $CO_2$ conditions. All experiments were performed at passage 3 to 5. HUVECs were seeded at $6 \times 10^4$ cells/2 mL density on 6-well plates (NUNC Inc, Naperville, Ill.). After allowing endothelial cells overnight for attachment, cells were ready for stimulation.

After washing with PBS, OxCL and reduced CL (20 ug/ml) were added. For annexin A5 (From Bender MedSystems GmbH, Austria) inhibition study, OxCL was incubated with Annexin A5 (10 ug/ml) for half hour before adding to cells. After 24 hours incubation, detached floating cells were washed away, cell were harvested into Falcon FACS tubes. After centrifuging at 1200 rpm for 5 minutes, cells were resuspended in 300 ul FACS buffer (1% FBS-PBS), incubated with 10 μl PE-conjugated anti-CD54 (eBioscience) and 10 μl FITC-conjugated anti-Human CD106 (Becton, Dickinson) for 30 minutes on ice. The intercellular adhesion molecule (ICAM-1) CD54 and the vascular cell adhesion molecule (VCAM-1) CD106 were studied with flow cytometry analysis equipped with CellQuest software. For each sample, 10,000 events were analyzed.

Macrophage Differentiation and Complement Induction

The macrophages which transformed from Human monocyte-derived THP-1 cells (American Type Culture Collection, Manassas, Va., U.S.A.) were plated in a 6-well plate at density of $1 \times 10^6$ cells/well in DMEM (INVITROGEN, USA) containing 10% FBS overnight. Then the cells were washed three times with serum free medium before incubated with OxCL (2 ug/ml), thereafter, the cells were washed ice-cold 4 times with 0.2% BSA/PBS and once with PBS. The cells were harvested in PBS containing 0.1% BSA and 0.01% NaN3. 10 ul monoclonal mouse anti-human C5b-9 (From Dakocytomation Demark) were added after incubation 30 minutes on ice, cells were centrifugated at 4° C. and supernatant were discarded, PBS containing 0.1% BSA and 0.01% NaN3 were added and 10 ul polyclonal rabbit anti-mouse IgG-FITC (Fab'2) (From Dakocytomation Demark) were added. Complement production was measured by flow cytometry (BD Biosciences, San Jose, Calif., USA). For each sample, minimum of 10.000 events was analyzed.

IL-6 Production

HUVEC cells from above were seeded at density $10^6/2$ ml into 6 well plates. Allowing cells attachment for 24 hours, OxCL (20 ug/ml) with or without Annexin A5 (20 ug/ml) and reduced CL were added and incubated for 24 hours. Cell supernatant were collected and IL-6 and IL-8 production were measured with protein multiplex immunoassay kits (from Bioscource, USA) and Bio-PIei™ system (BioRad, USA).

Enzyme-Linked Immunosorbent Assay (ELISA) for Annexin A5 Binding

F96 microtiter polysorp plates (Roskilde Denmark), were coated with OxCL, CL or Hydro Heart cardiolipin (Biosearch Technologies, Inc, Ca, USA) 10 μg/ml incubated overnight at 4° C. After five washings with PBS, the plates were blocked with 2% PBS-BSA for 2 h at room temperature. Annexin A5 were added and incubated for 1 hour. After washing, bound annexin A5 was detected by incubating subsequently with rabbit anti-human annexin V polyclonal antibodies (Hyphen Biomed, Andresy, France) 1:2000 and polyclonal goat anti-rabbit Immunoglobulins/AP (DakoCytomation) 1:3000 were used. The reaction was developed with alkaline phosphatase substrate (Sigma), and optical density (OD) was read at 405 nm with an ELISA Multiscan Plus spectrophotometer (Molecular Devices Emax, San Francisco). All samples were measured in duplicates and the coefficient of variation was below 15%.

Use of other suitable monoclonal or polyclonal antibodies for detecting bound annexin V is also possible.

Labeling OxLDL with DiI

OxLDL (Industrylane Frederick) were incubated with DiI (Molecular Probes Engene, Oregon, USA) in lipoproteindeficient serum (Sigma) at 37° C. for 15 hours. Then dialyzed against saline-EDTA buffer for 6 hours.

Uptake of Dil-labeled OxLDL

Uptake of Dil-labelled OxLDL was studied either by Flow cytometry or Fluorescence/confocal microscopy. For microscopy, The macrophages $1\times10^6$ were grown overnight on culture slides (Nunc, Naperville, N.Y.), For flow cytometry, The macrophages were plated in a 6-well plate at density of $1\times10^6$ cells/well in DMEM (INVITROGEN, USA) containing 10% FBS overnight. Then the cells were incubated with Dil-OxLDL (5 μg/ml), with OxCL (40, 80 μg/ml), with CL control (40, 80 μg/ml), with unlabeled OxLDL (40 μg/ml) or with unlabeled LDL (40 μg/ml) for 4 hours. For Annexin A5 inhibition of Dil-OxLDL experiment, macropages were incubated with Dil-Ox-LDL (5 ug/ml), with Annexin A5 (0.01, 0.04, 0.16, 0.64, 1, 10, 20, 40 ug/ml). Thereafter, the cells from above were washed 4 times with 0.2% BSA/PBS and once with PBS. The cells were harvested in PBS containing 0.1% BSA and 0.01% NaN3. Mean fluorescence intensity was measured by flow cytometry (BD Biosciences, San Jose, Calif., USA). For each sample, fluorescence emission above 550 nm was measured and a minimum of 10.000 cells was analyzed.

Cell Culture

Human mononuclear cells were isolated from freshly prepared buffy coats (Karolinska Hospital blood bank, Stockholm, Sweden) by gradient centrifugation on Ficoll-Paque (Amersham Biosciences, Uppsala, Sweden). The mononuclear cells were cultured at a density of $5\times10^6$/ml in RPMI-1640 medium with 25 mM Hepes, 1% L-glutamine, 1% penicillin-streptomycin and 10% FBS. After 7 days, there are proximate $2\times10^6$ macrophages per well.

Isolation of Polymorphonuclear Neutrophils (PMNs)

Human PMNs were isolated from freshly prepared buffy coats (Karolinska Hospital blood bank, Stockholm, Sweden) by dextran sedimentation, hypotonic lysis of erythrocytes and gradient centrifugation on Lymphoprep (Axis-Shield PoC AS, Oslo, Norway). PMNs were suspended at a density of $10\times10^6$/ml in Dulbecco's PBS (Gibco (Invitrogen), Paisley, UK). PMN purity (>95%) and viability (>98%) was determined using Hemacolor (J. T. Baker, Utrecht, Holland) and Trypan Blue (Sigma Chemical Co.) staining, respectively.

Intracellular Calcium Mobilization

Neutrophils were added into black, 96-well plates with transparent bottom (Corning Costar; $5\times10^4$ cells/well), and spin down the plate at 120×g for 3 min, afterwards changing the medium containing 4 μM FURA-2AM (Fura-2 acetoxymethyl ester), or buffer as appropriate, and the cells were incubated for 30 min at 37° C. and 5% $CO_2$. Cells were washed four times with 50 μl of a buffer solution (135 mM NaCl, 4.6 mM KCl, 1.2 mM $MgCl_2$, 1.5 mM $CaCl_2$, 11 mM glucose, 11 mM Hepes, pH 7.4) before a final 45 μl volume of buffer was added to each well.

The plates were transferred to a fluorometer (Fluostar™, BMG Technologies), and 50 μl of different agonists according to experimental designs or buffer solution as control were injected into individual wells and the cells were monitored for the next 120 seconds. Control wells containing cells that had not been exposed to FURA-2AM were used to subtract background auto-fluorescence. The results are given as the ratio of mean fluorescence intensity (MFI) between 340 and 380 nm, and normalized by control.

Analysis of leukotriene $B_4$ Biosynthesis by EIA kit $2\times10^6$ macrophages were incubated with different agents according to the experimental design, and then quenched with an equal volume methanol. After acidified to pH 3-4, the samples were purified by solid-phase extraction (Supelclean™ LC-18, Supelco) and eluted in methanol. After dried under nitrogen, the samples were re-suspended in EIA buffer. The level of $LTB_4$ was determined with $LTB_4$ EIA kit (Cayman Chemical) by using dilutions within the linear portion of the standard curve.

Ultrasound Scan for Assessing FMD and NTG Induced Vasodilatation

All ultrasound scans were made using a duplex scanner (Acuson Sequoia, Mountain View, Calif., USA) with a 8 MHz ART linear array transducer in a quiet semi-darkened room with the subject in the supine position. Scans were videotaped for off line analysis. Subjects were asked not to smoke, and not to drink coffee or tea for at least 2 h before the study. All studies were done by the same operator using the same equipment. All measures were done off-line from digitalised cine-loops by one measurer.

The brachial artery was scanned longitudinally 2-10 cm above the elbow, with the vessel placed horizontally across the screen. Settings were made to optimise lumen-arterial wall interface, and thereafter not changed during the study. The transducer was held in the same position throughout the study by a mechanical arm. A resting B-mode scan was recorded, flow velocity was measured with a 5 MHz pulsed Doppler with a 1.5 mm gate width in the centre of the vessel at a 70 degree angle. Flow-increase was induced by the post ischemic response to deflation of a pneumatic tourniquet placed around the forearm of the patient to 250 mmHg for 4.5 min. A second scan was recorded from 30 s before to 90 s after cuff deflation. Flow velocity was recorded with a pulsed wave Doppler for 15 s before and 15 s after cuff deflation. This was followed by 10 minutes rest for vessel recovery. A third scan at rest was taken and 0.40 mg sublingual nitro-glycerine spray was administered. Three to four minutes after nitro-glycerine the last scan was recorded. The vessel was measured at a fixed point in all scans. Measures were made on digitalised cone-loops from the anterior wall leading edge of the intima-media echo to the leading edge of the far wall intima-media Nessel interface incidentally with the R-wave on the ECG for three consecutive cardiac cycles and the average measurements were used. After reactive hyperaemia, measurements were made 50-70 s after cuff deflation. The increase in vessel diameter during hyperemia and after nitro-glycerine administration is expressed as percentages of the first control scan.

Determination of Anti-OxCL Antibody Levels

The Immulon 1B plate was coated with 50 μl/well of OxCL 10 μg/ml, and allowed to dry overnight at 4° C. After washing with PBS, the plate was blocked with 2% BSA at room temperature for 2 hours. 1:50 diluted sera were added in duplicates. The plate was incubated overnight at 4° C. The secondary antibody (anti-Ig) was added 100 μl/well, then left overnight at 4° C. Then five times Washing with PBS, Substrate was added 100 μl/well, The ELISA Multiscan Plus Spectrophotometer was used to determine optical density.

TNF Production

The PBMC were cultured in 96-well culture plates at density of $2*10^5$ cells/100 ul/well with stimulation of 1 ug/ml PHA in medium presence with different sera for 48 hours, and the supernatants were measured for TNF-a concentration by commercially available ELISA kits.

Extraction of Anti-OxCL IgG from Intravenous Immunoglobulin (IVIG)

OxCL-MBSA and MBSA were coupled to a HiTrap NHS column (Amersham Biosciences) separately according to the manufacturer instruction.

Human pooled immunoglobulin (IVIG; Gammaguard, S/D) was diluted in binding buffer (20 mM $Na_2HPO_4$) at 50 mg/ml and filtered through 0.45 µm filter before passing through pre-coupled OxCL-MBSA and MBSA Sepharose gel column. anti-OxCL IgG was eluted by 0.1M Glycin-HCl buffer. The purified fractions were desalted using PD-10 columns (Amersham Pharmacia Biotech AB). Binding to oxCL (as described for determination of anti-oxCL antibodies) was confirmed.

Adhesion Molecule Expression by Endothelial Cells—Inhibition by Extracted Anti-OxCL Pooled human umbilical vascular endothelial cells (HUVECs) at passage 2 were purchased from Cascade Biologics, Inc (Portland, Ore). Cultures were maintained in EGMTM phenol red-free medium (Clonetics, San Diego, Calif.), containing 2% of fetal bovine serum and supplements, at 37° C. under humidified 5% CO2 conditions. All experiments were performed at passage 3 to 5. HUVECs were seeded at 6×104 cells/2 mL density on 6-well plates (NUNC Inc, Naperville, Ill.).

After allowing 24 hours for cells attachment, the cells were incubated with oxidized cardiolipin (oxCL) 10 µg/ml either with or without anti-oxCL-IgG 0.22 mg/ml. After 24 hours incubation, detached floating cells were washed away, cell were harvested into Facoln FACS tubes. After centrifuging at 1400 rpm for 5 minutes, cells were resuspended in 300 ul FACS buffer (1% FBS-PBS), incubated with 10 µl FITC-conjugated anti-Human CD106 (Becton, Dickinson) for 30 minutes on ice. The vascular cell adhesion molecule (VCAM-1) CD106 were studied with flow cytometry analysis equipped with CellQuest software. For each sample, 10,000 cells were analyzed.

DRAWINGS

Figure 1B:
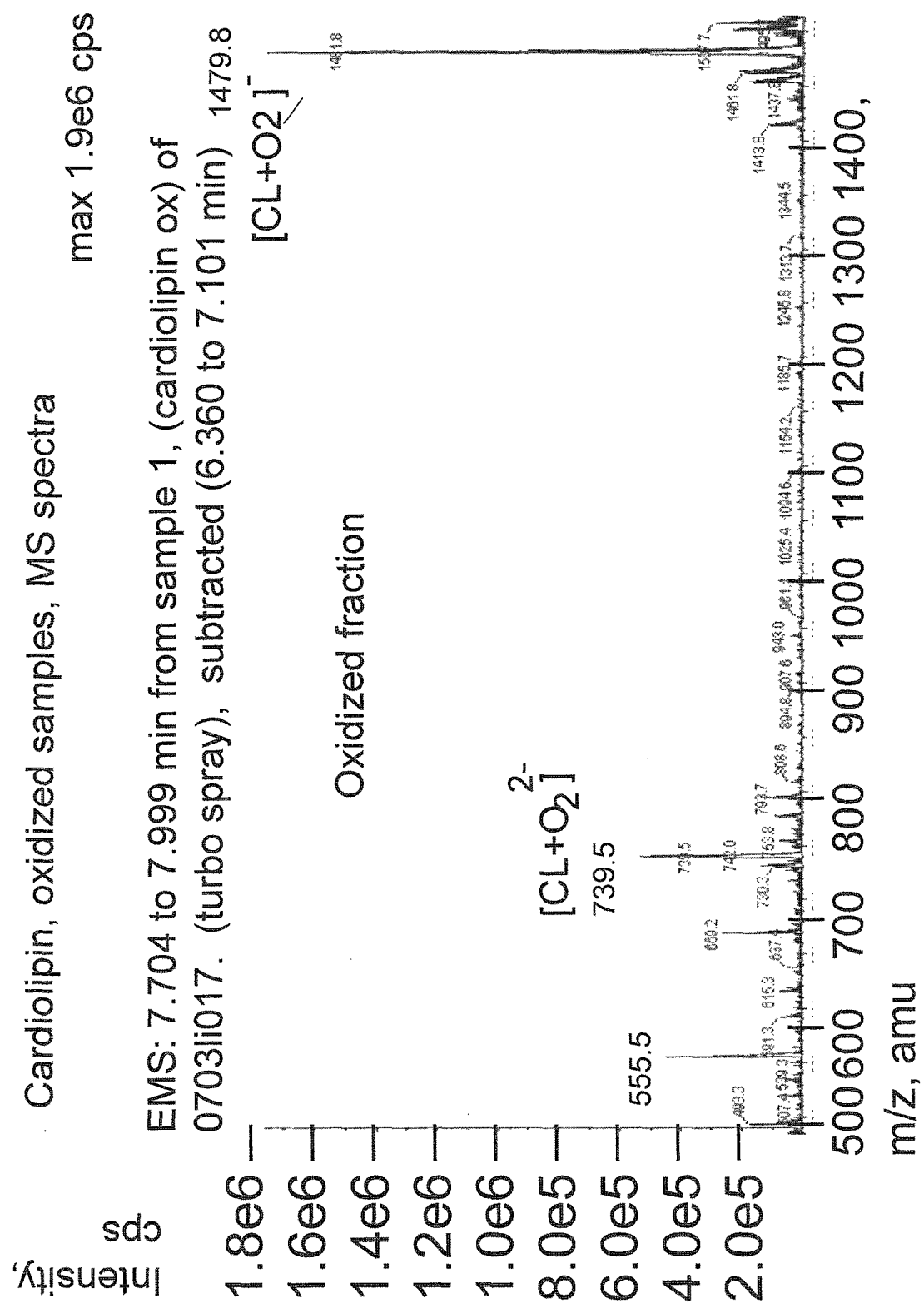

FIGS. 1A and 1B: Electrospray ionization mass MS spectrometer (Micromass, Beverly, Mass.) was used to demonstrate that bovine heart cardiolipin was oxidized.

Figure 2:
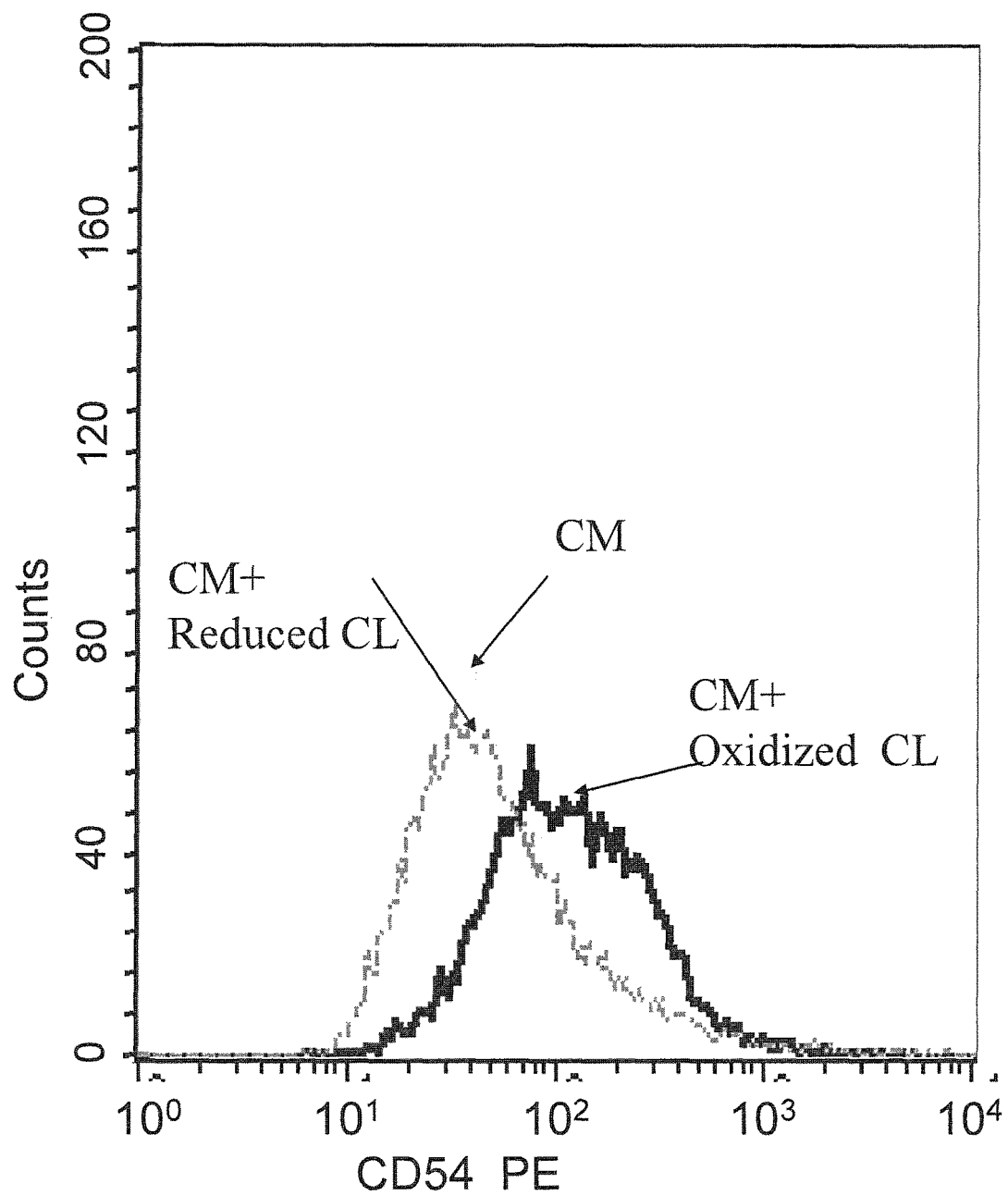
Figure 2:
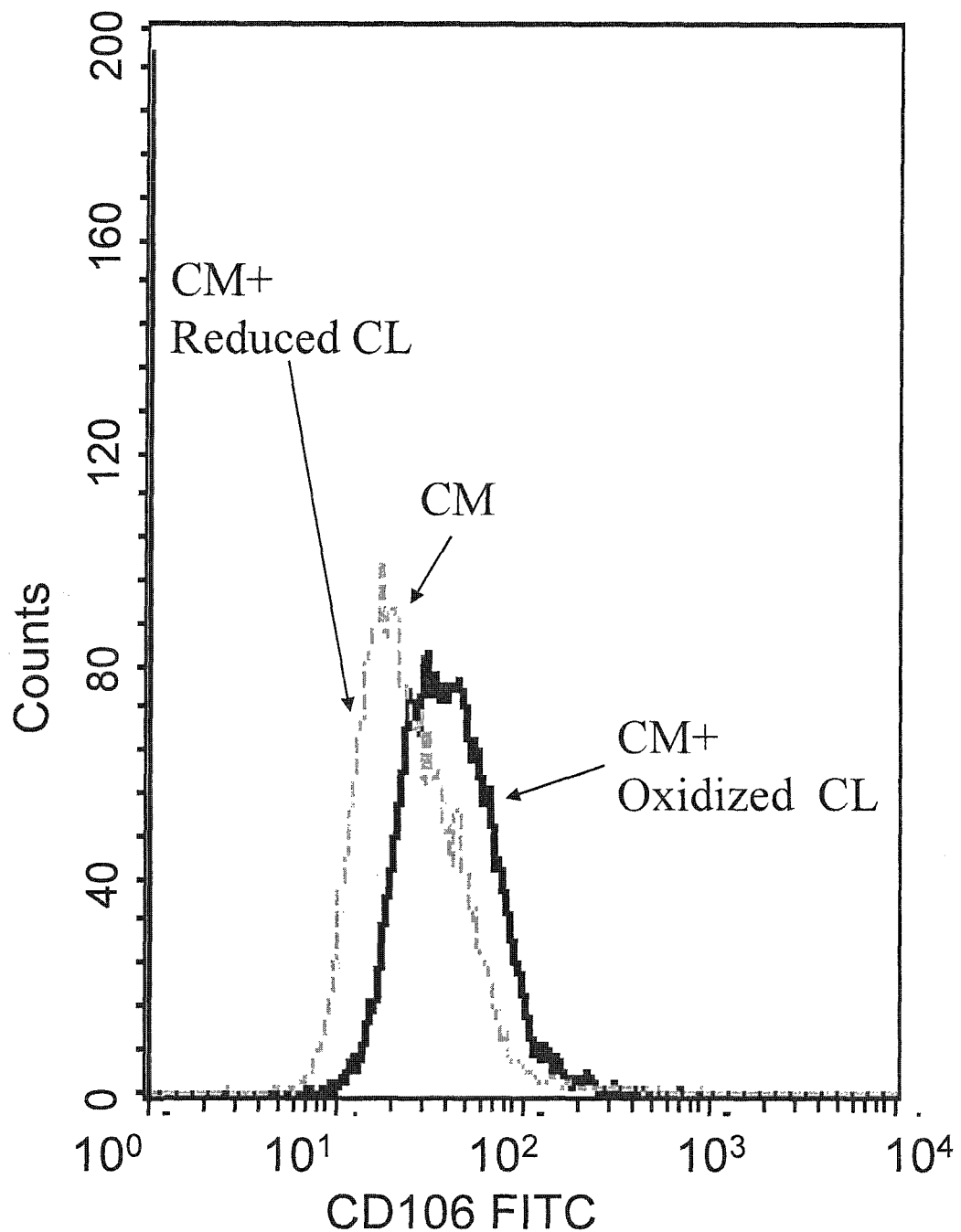

FIGS. 2A and 2B: Induction of adhesion molecules. Oxidized CL but not CL induces adhesion molecules in endothelial cells, flow cytometry.

Endothelial cells were incubated with Oxidized CL (20 ug/ml) or CL (20 ug/ml) for 24 hours, oxidized CL induced ICAM-1 and VCAM-1 production but CL does not show same effect.

Figure 3:
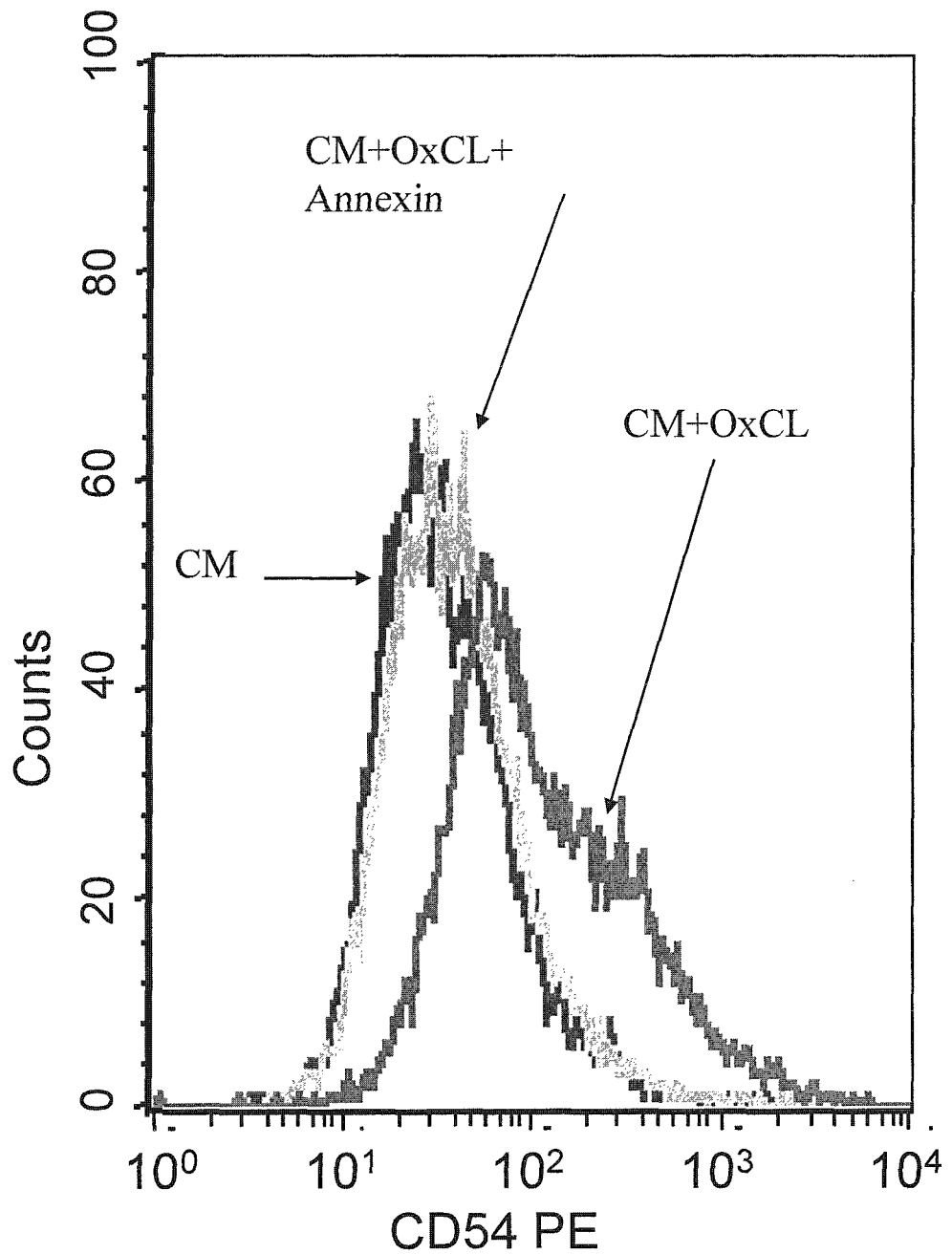
Figure 3:
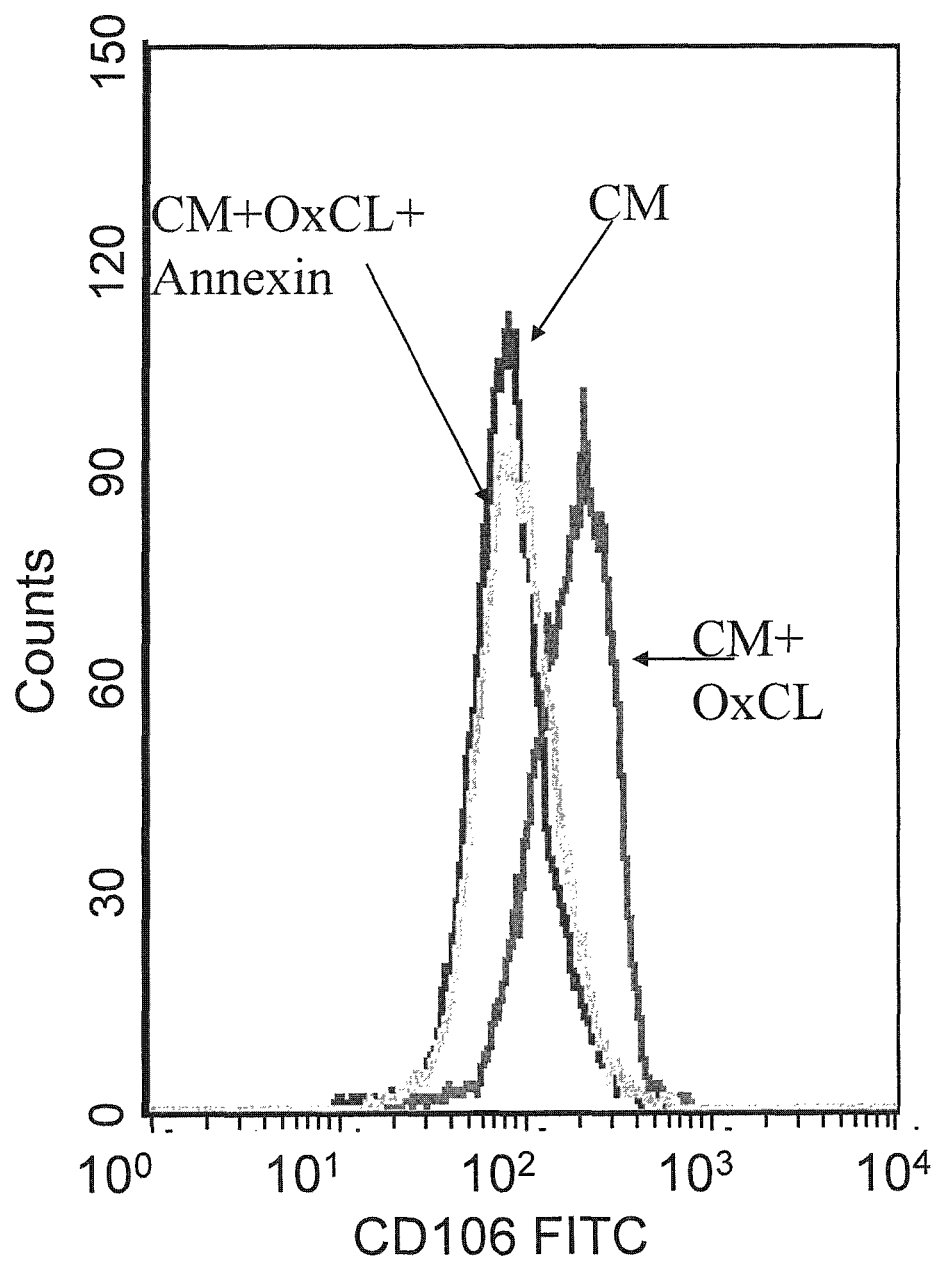

FIGS. 3A and 3B: inhibition of oxCL-induced adhesion molecule expression by Annexin A5, detected by Flow cytometry.

Oxidized CL (20 ug/ml) was preincubated with Annexin A5 (10 ug/ml) before stimulating cells for 24 hours. Annexin A5 inhibited oxCL induced endothelial cell expression of ICAM-1 (CD54) and VCAM-1 (CD106).

Figure 4:
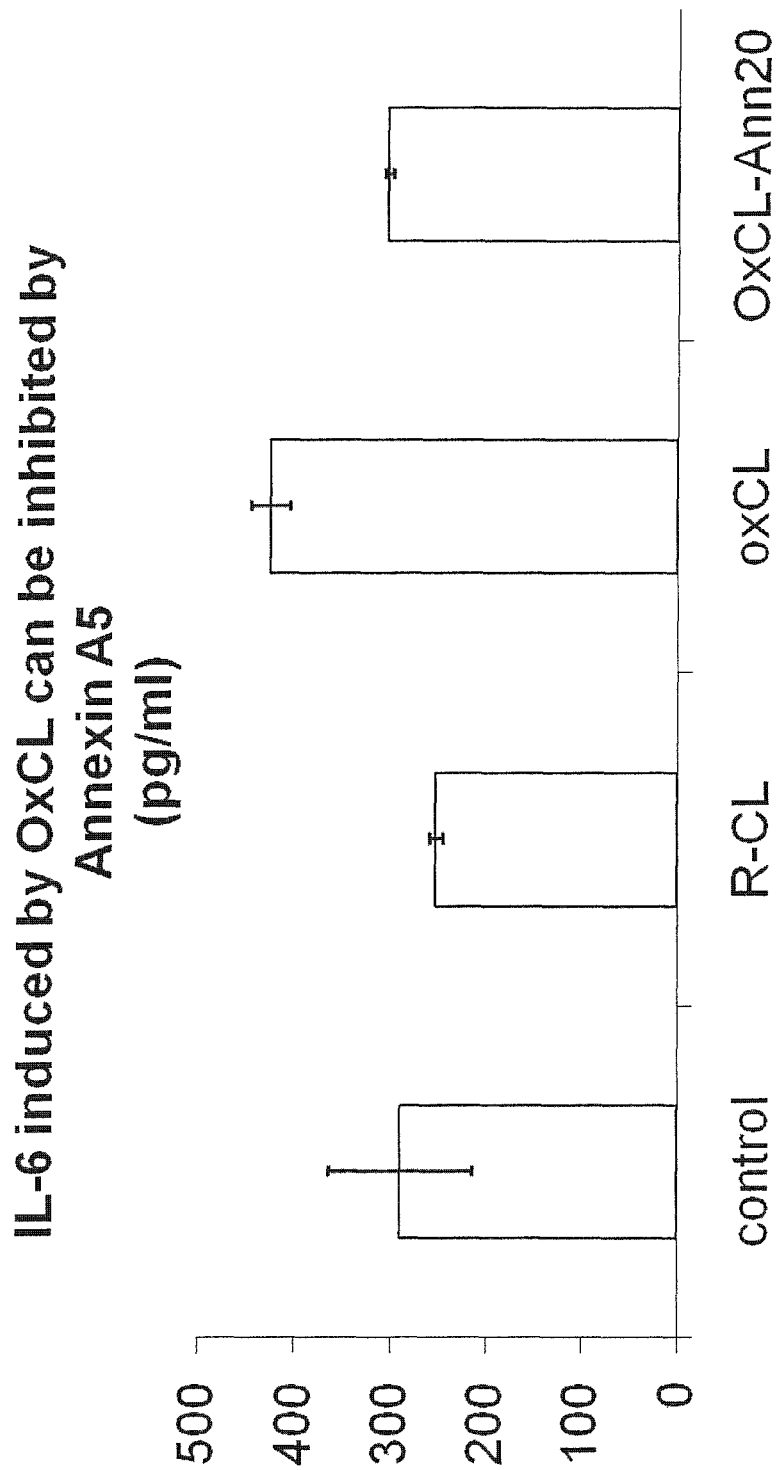

FIG. 4: Induction of IL-6 by oxCL and inhibition by Annexin A5. determined by Luminex. Detected by intensity of fluorescence.

Endothelial cells were incubated with OxCL (20 ug/ml) with or without Annexin A5 (20 ug/ml) and CL (20 ug/ml) for 24 hours, oxidized CL can significantly induce IL-6 production and this effect can be inhibited by Annexin A5. CL had no such effect.

Figure 5:
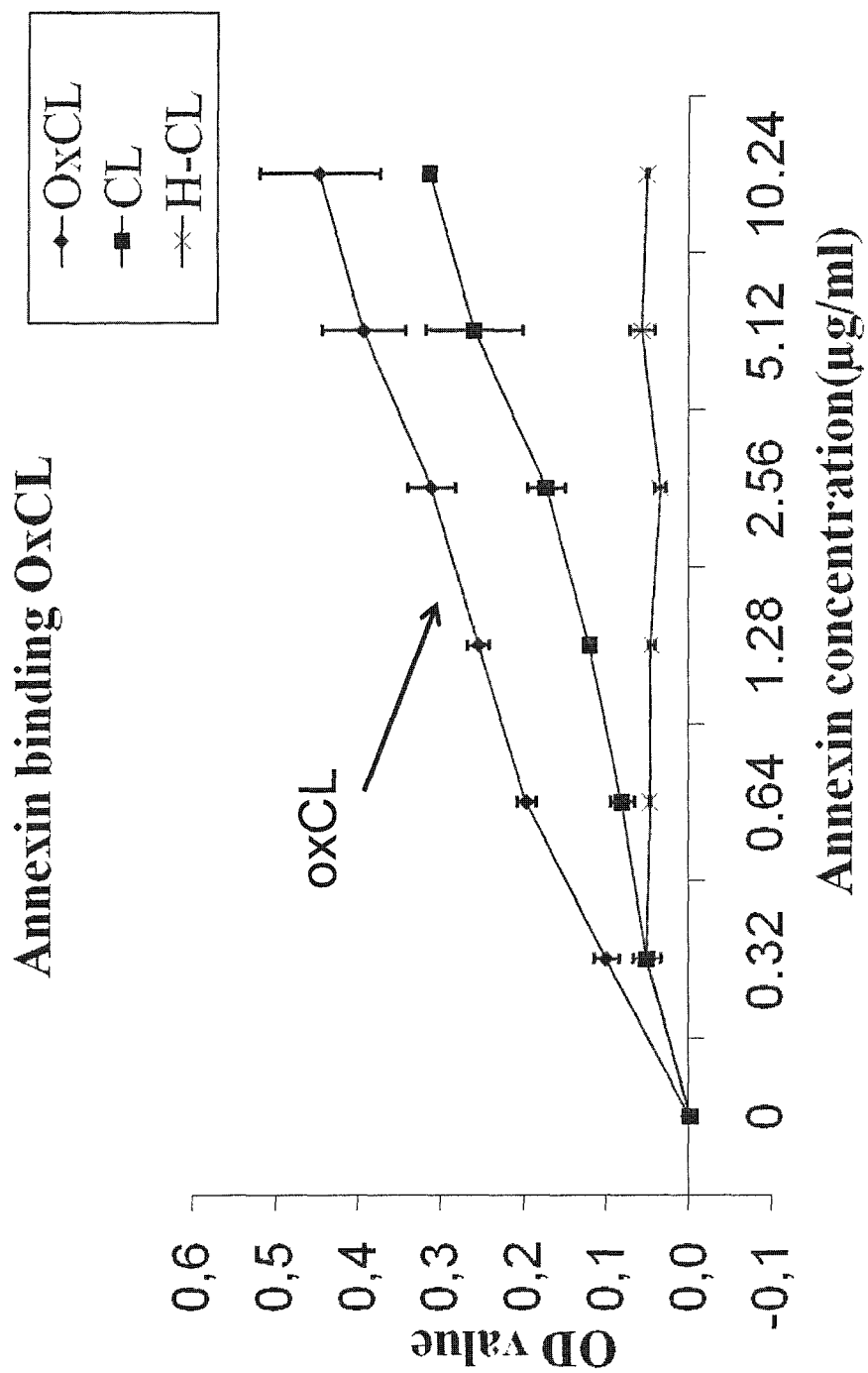

FIG. 5: Binding of oxCL by Annexin A5, ELISA.

OxCL, CL and reduced CL (5 ug/ml) were coated on ELISA plates overnight. Annexin A5 (0.32 ug/ml, 0.64 ug/ml, 1.28 ug/ml, 2.56 ug/ml, 5.12 ug/ml and 10.24 ug/ml) can bind to oxidized cardiolipin and air exposed CL but not reduced cardiolipin.

Figure 6:
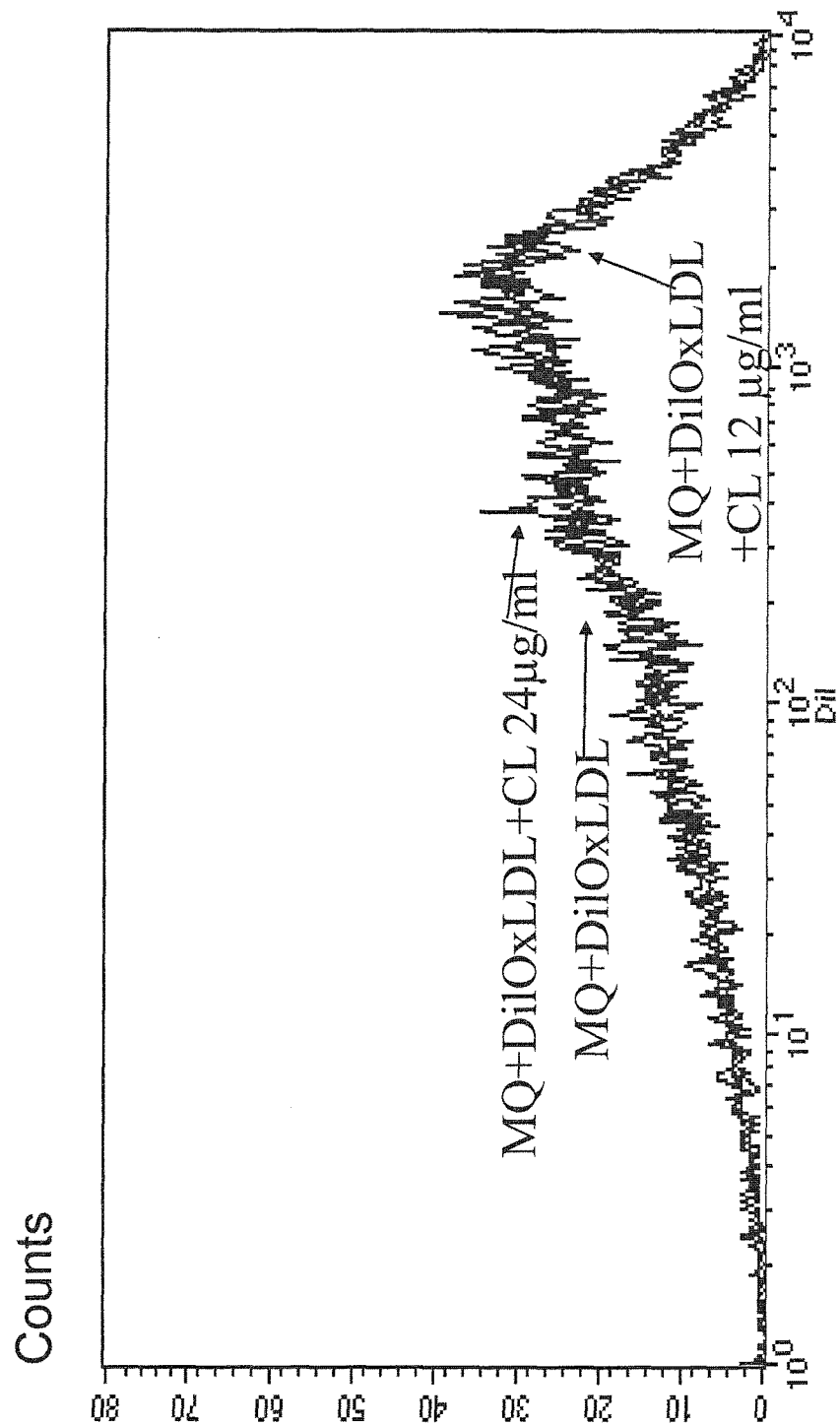
Figure 7A:
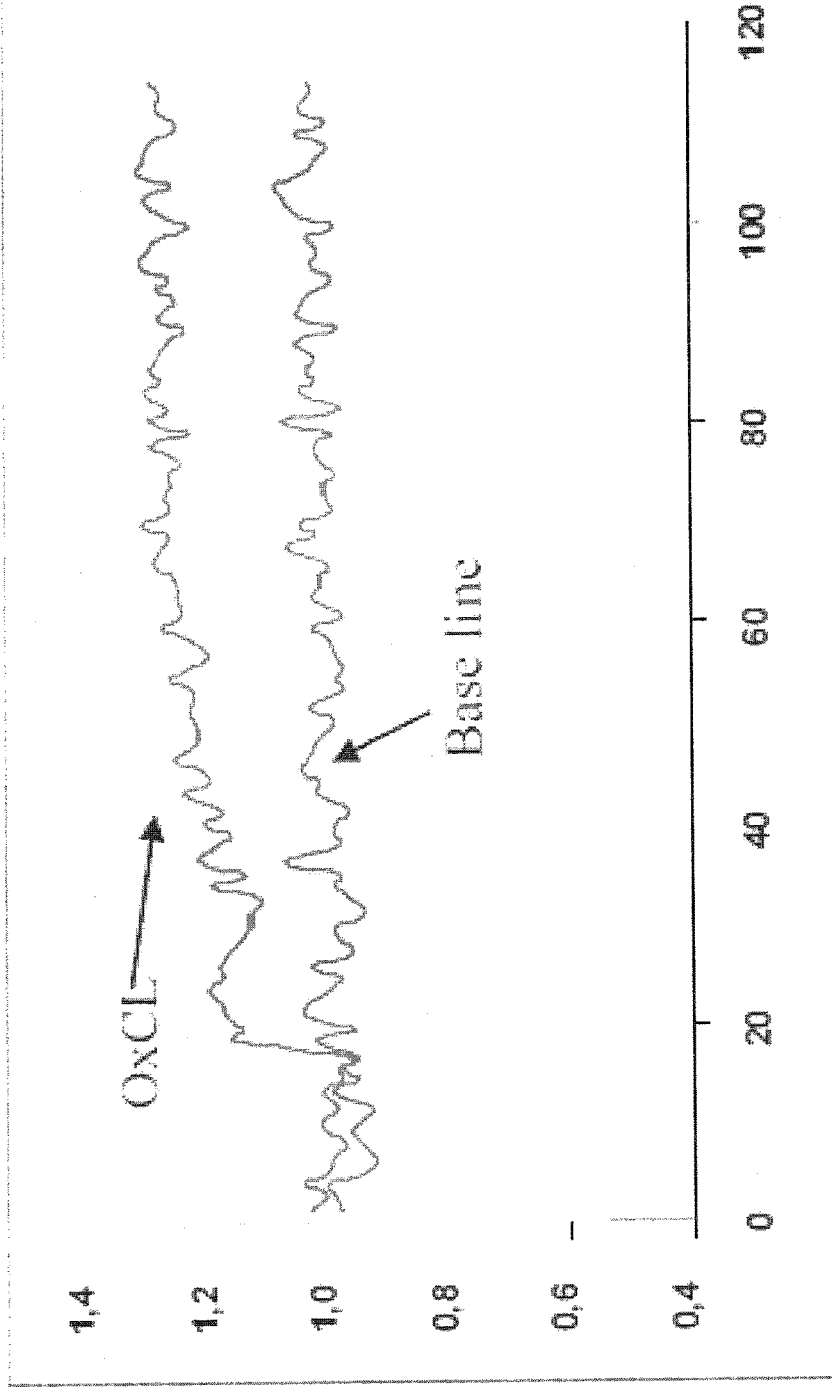
Figure 7:
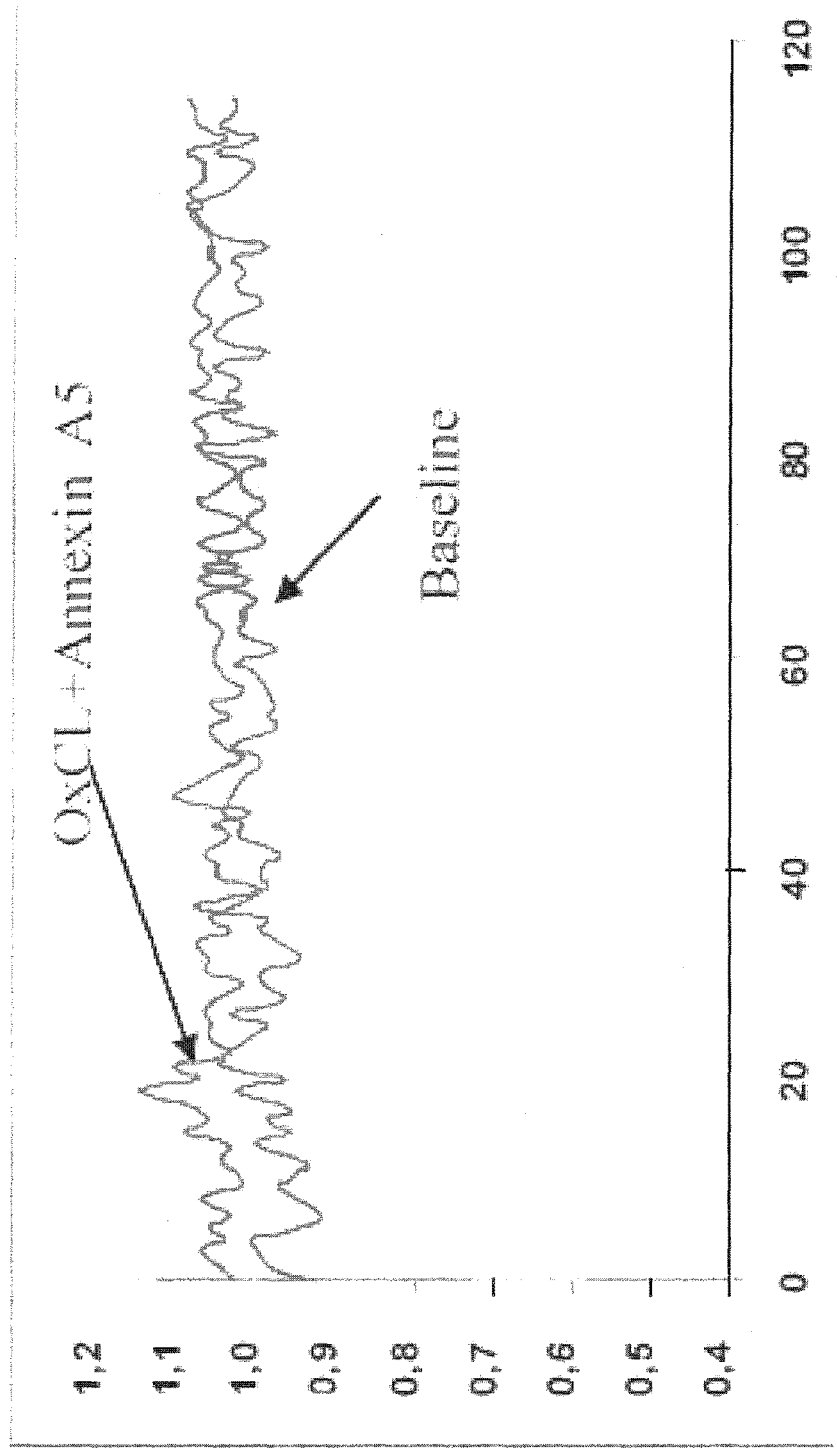
Figure 7:
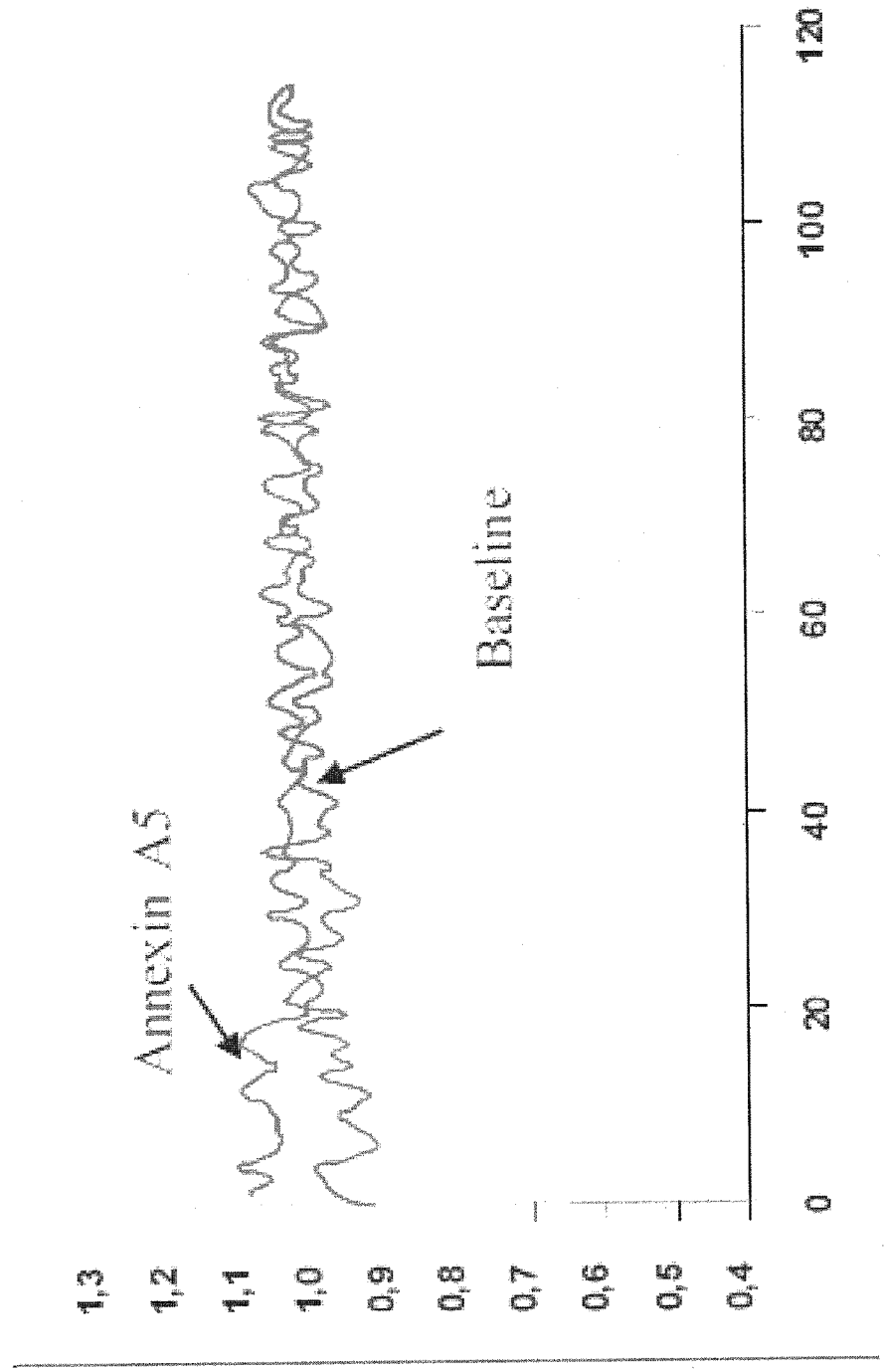
Figure 7:
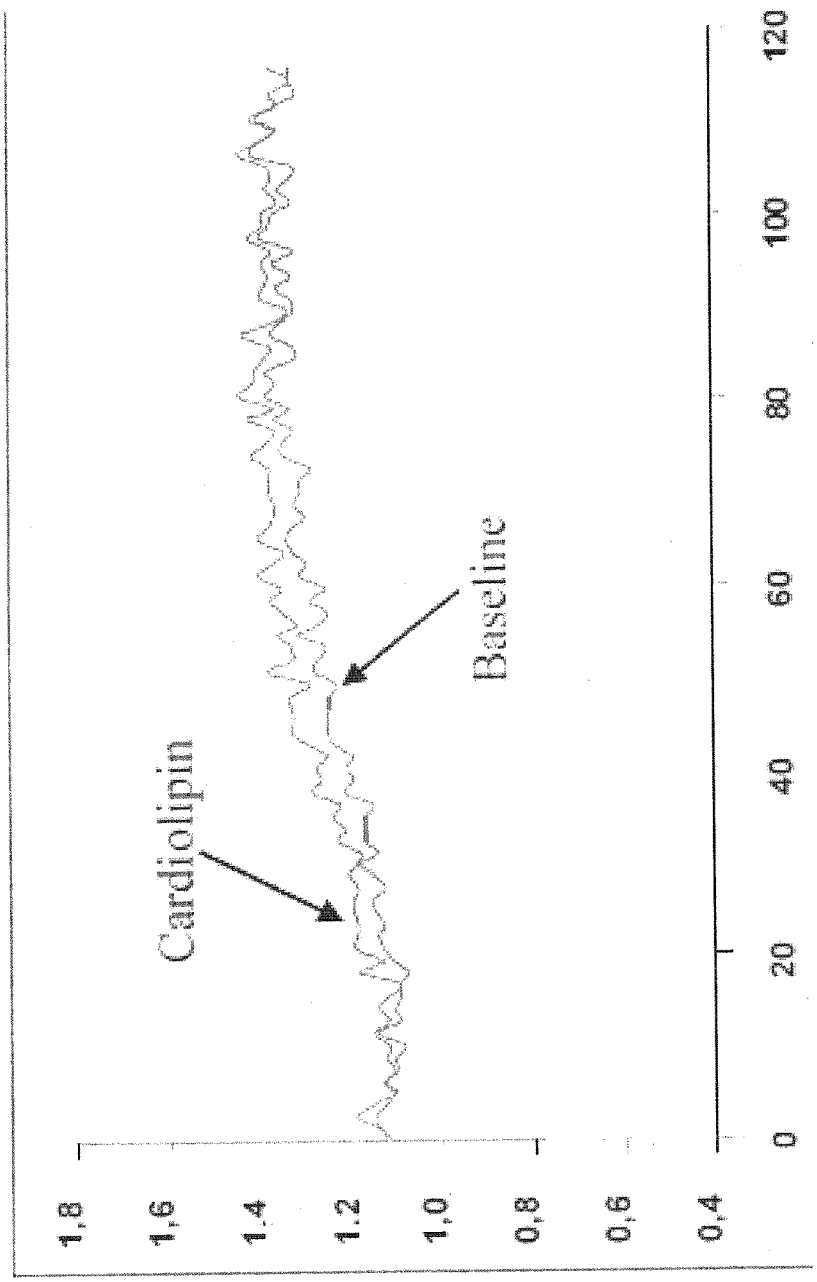

FIGS. 6A and 6B: Effect of oxCL on uptake of oxLDL in macrophages, detected by Flow cytometry.

OxCL competed macrophage uptake of OxLDL, but CL did not have such effect. (Human acute monocytic leukemia cell line) THP-1, cells differentiated MQ were studied uptake of dil-OxLDL, the uptake could be competed by OxCL but not non-oxidized CL.

FIGS. 7A, 7B, 7C and 7D: oxCL-induced calcium mobilization, Fluorometer.

Results shows that only oxidized cardiolipin can activate the neutrophils and induce the intracellular calcium mobilization. Furthermore, annexin can prevent the effects of oxCL on neutrophils.

Figure 8:
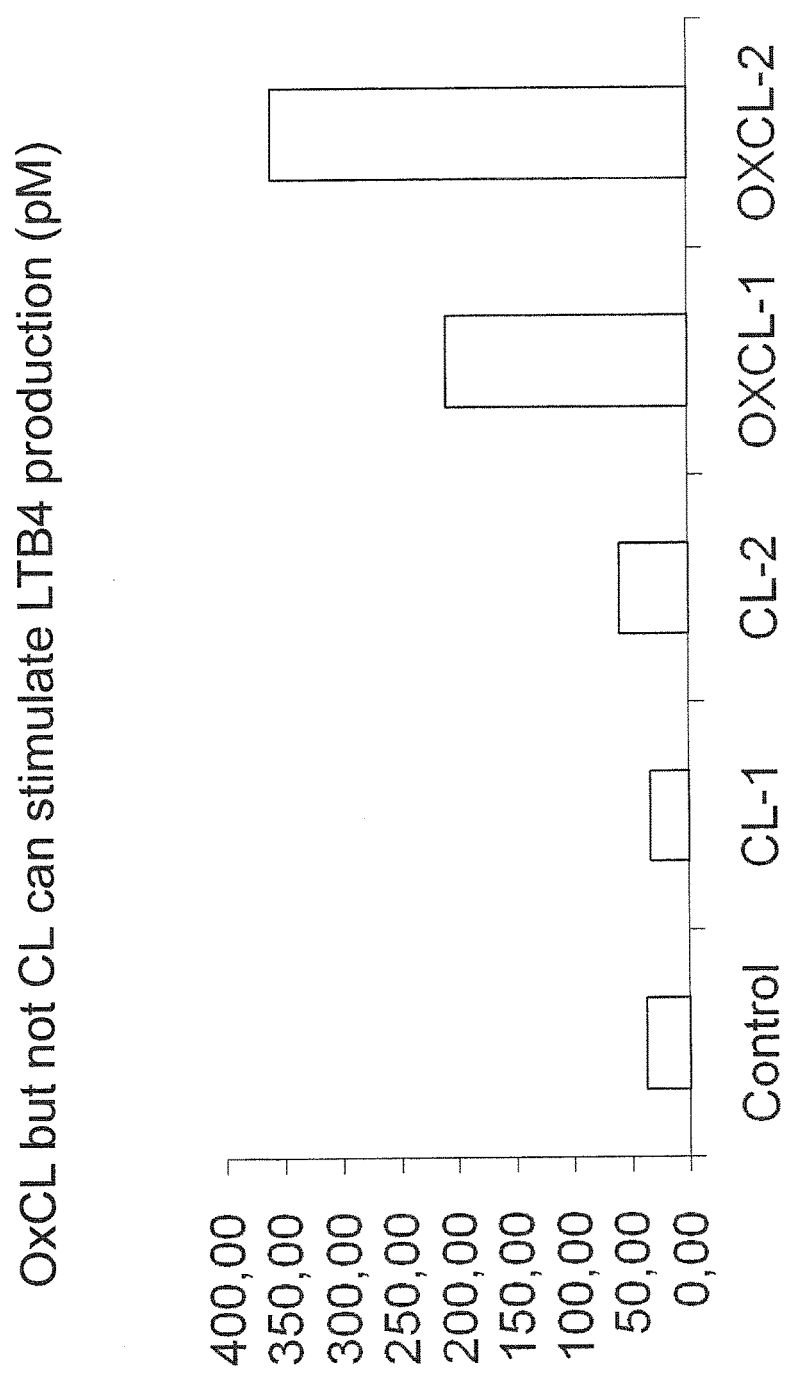

FIG. 8: Effect of oxCL on leukotriene B4 release, EIA. Oxidized cardiolipin promotes human neutrophils and macrophages to release leukotriene $B_4$, but cardiolipin did not show the similar reaction.

Figure 9:
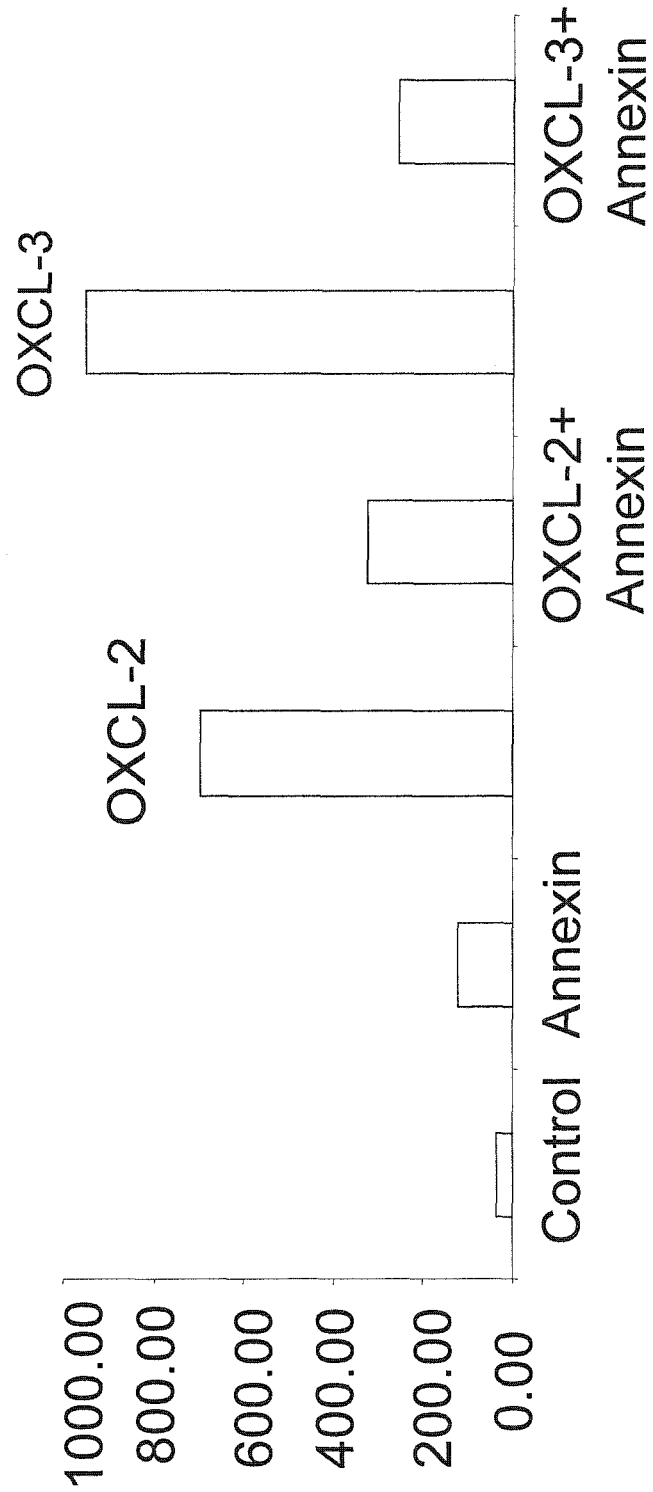

FIG. 9: Effect of Annexin A5 on oxCL induced $LTB_4$ production from oxCL-stimulated human neutrophils and macrophages, which may give new insights into clinical novel targets for medical treatments of the associated inflammatory conditions, EIA.

Figure 10:
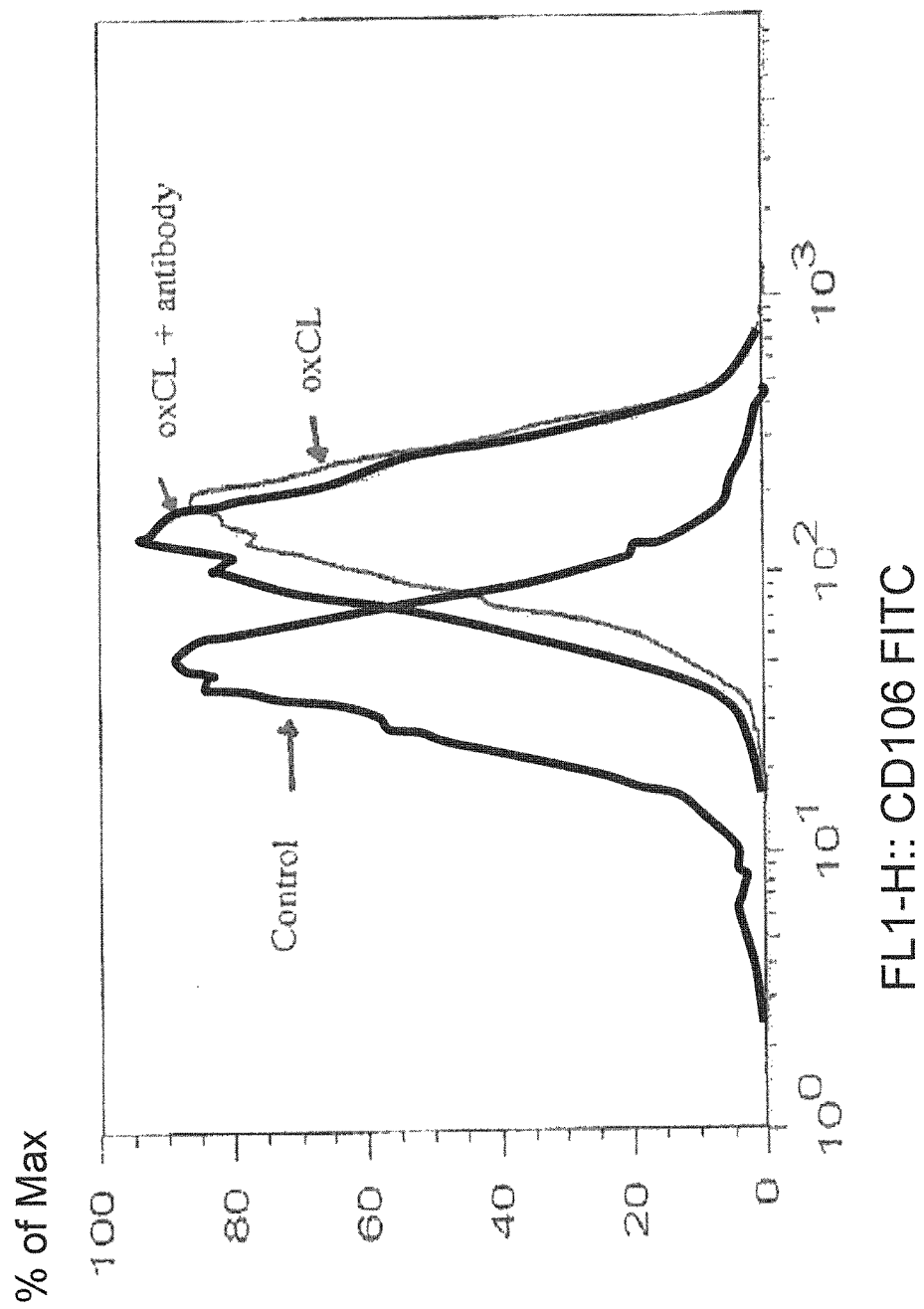

FIG. 10: Antibodies against oxCL were extracted from human Ig and incubated with oxCL. Experiment indicates that such extracted anti-OxCL decrease effects of oxCL, as seen by a shift to the left of the histogram.

FIGS. 11A, 11B, 11C, 11D, 11E and 11F: Effects of oxCL on activation of T-cells, flow cytometry.

Figure 11:
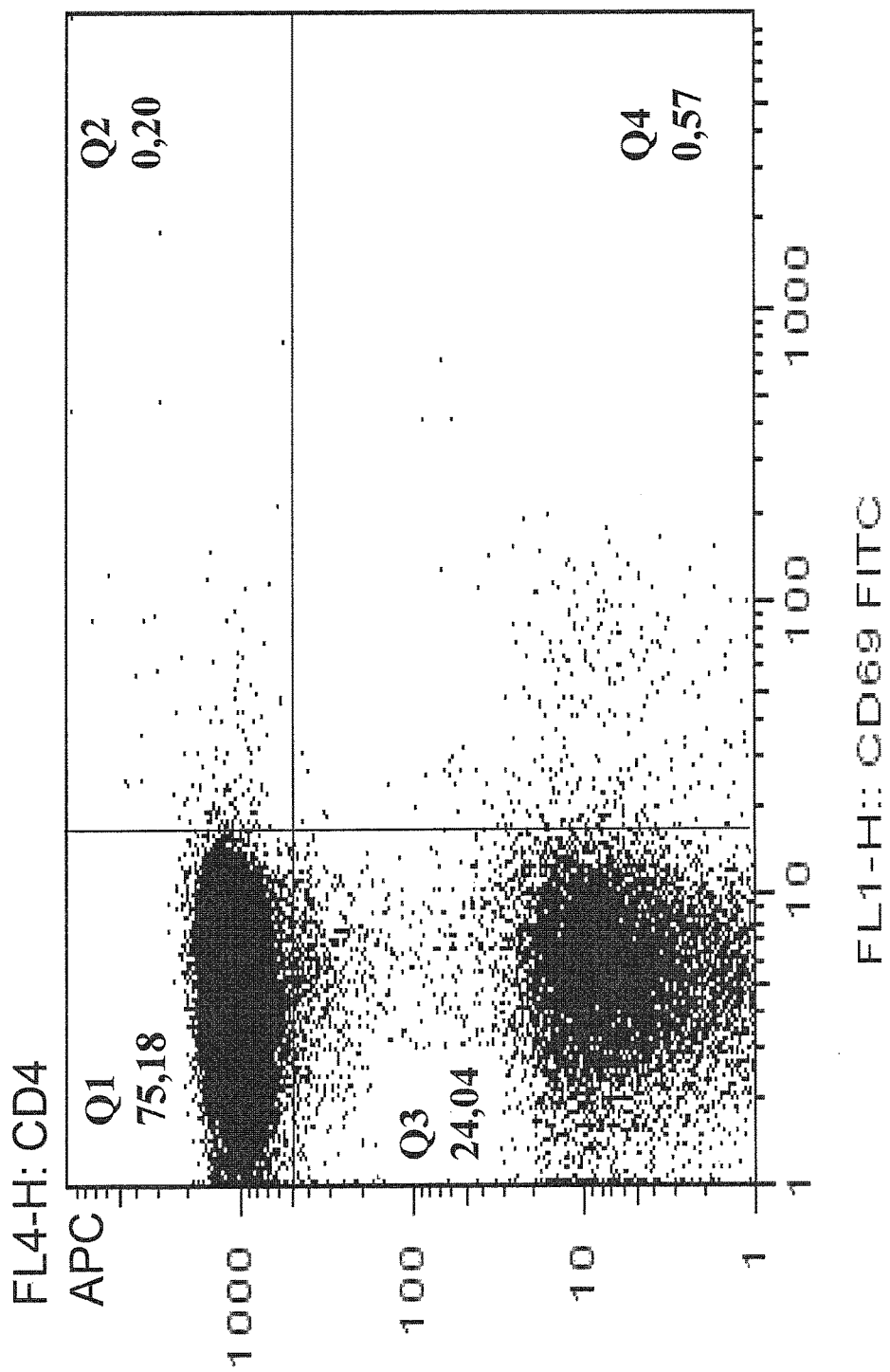
Figure 11:
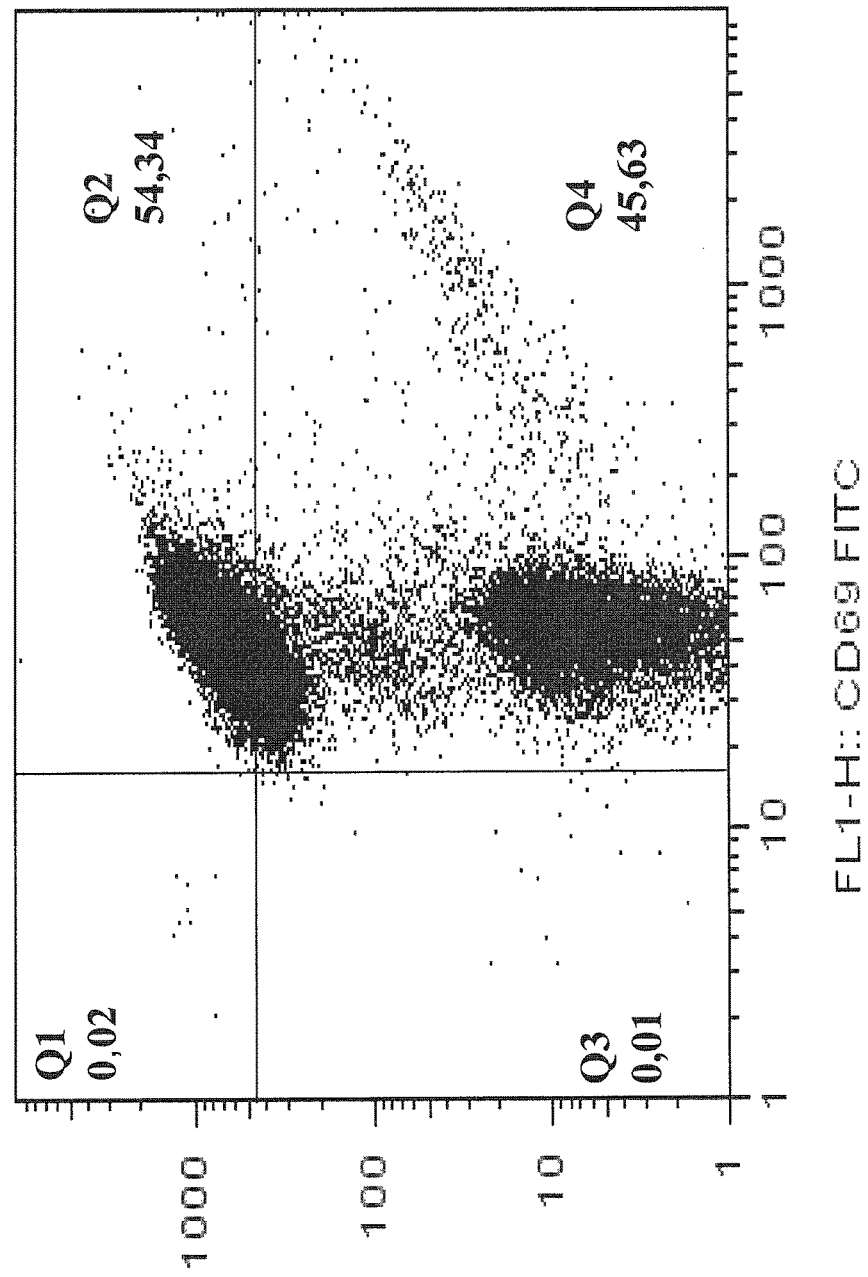
Figure 11:
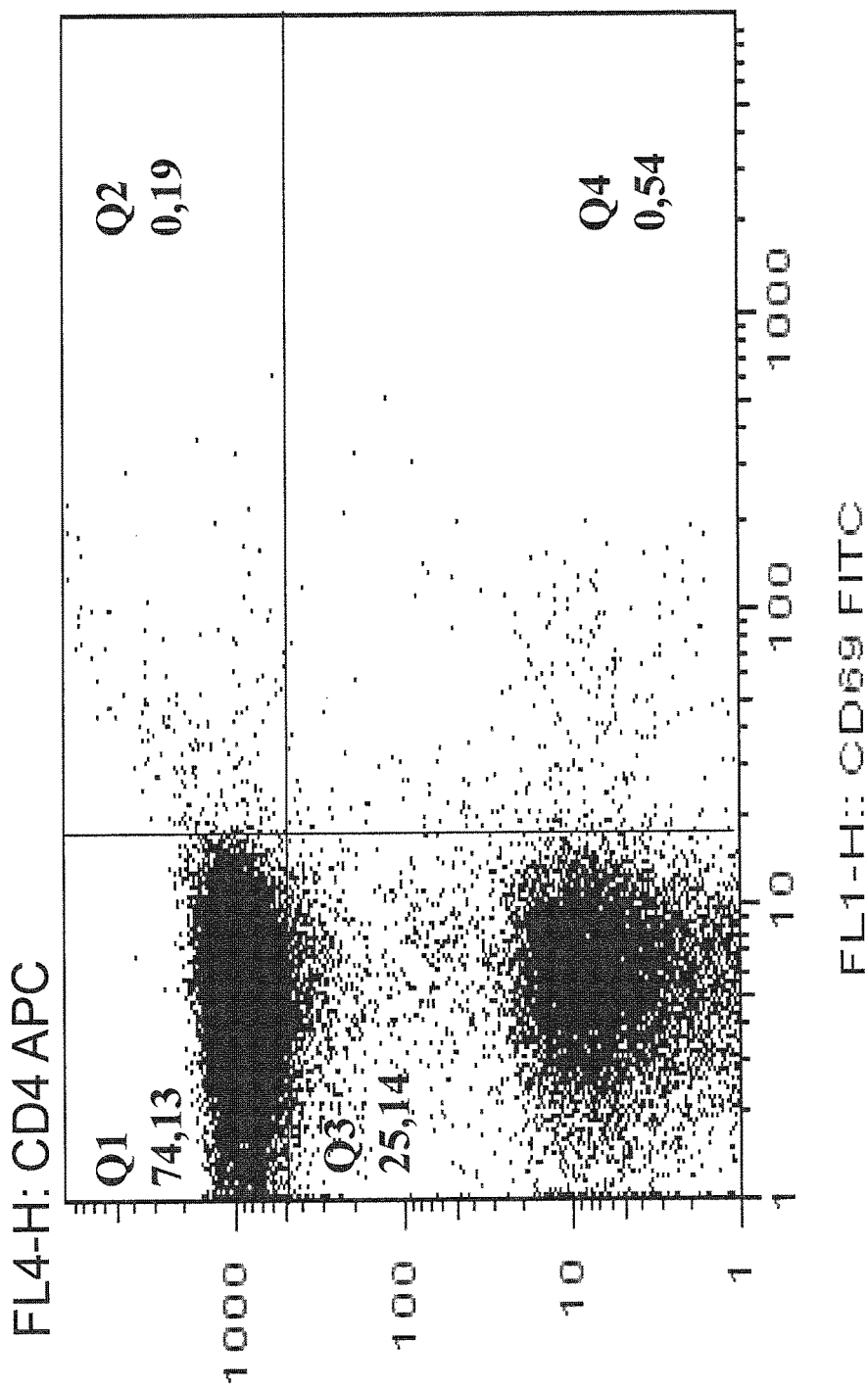
Figure 11:
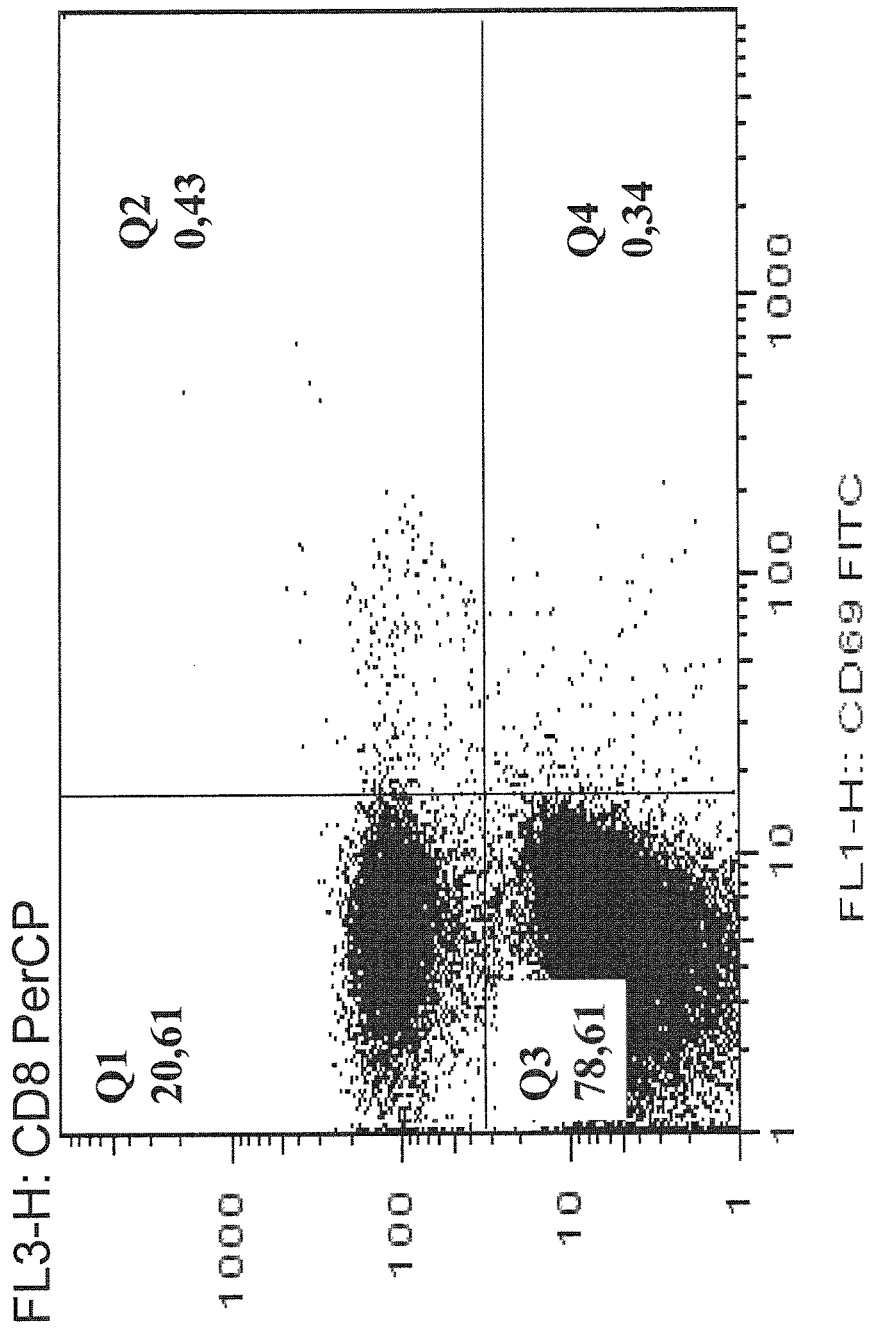
Figure 11:
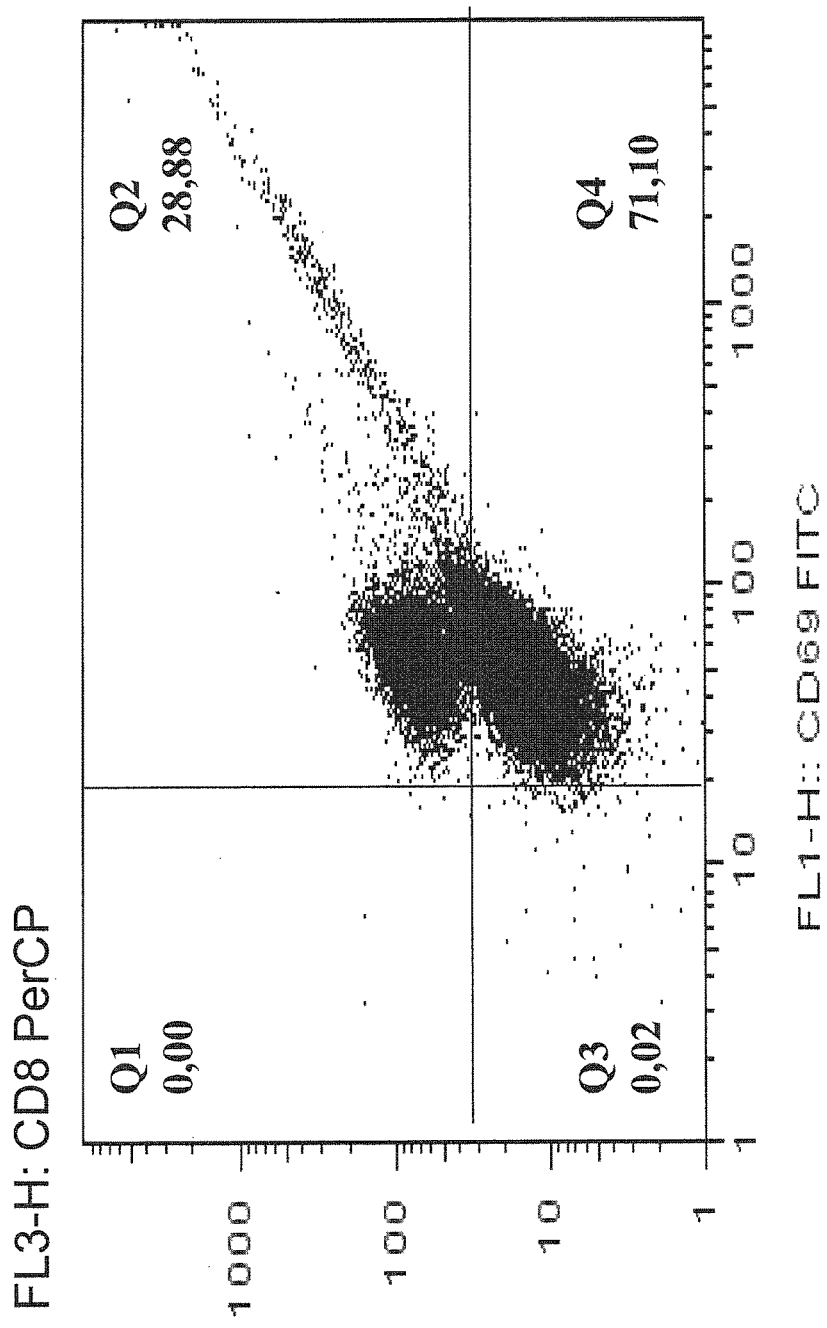
Figure 11:
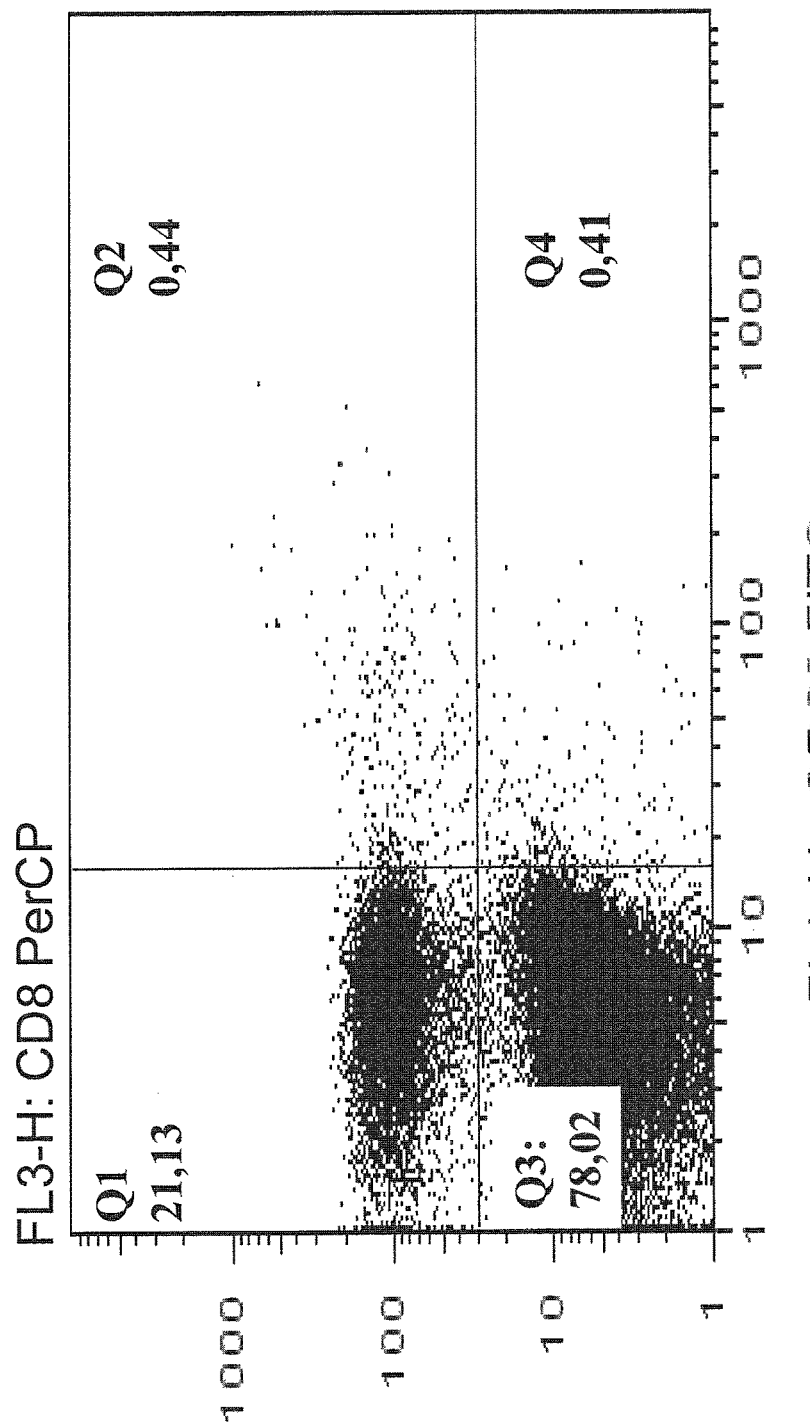

FIG. 11A: Effects on CD4-positive T-cells, control

FIG. 11B: Effects on CD4-positive T-cells, 5 µg/ml of oxCL

FIG. 11C: Effects on CD4-positive T-cells, 5 µg/ml of CL (native, non-oxidized CL)

FIG. 11D: Effects on CD8-positive T-cells, control

FIG. 11E: Effects on CD8-positive T-cells, 5 µg/ml of oxCL

FIG. 11F: Effects on CD8-positive T-cells, 5 µg/ml of CL

Human PBMC (Peripheral blood mononuclear leukocytes) were incubated over night with 5 µg/ml of oxCL or CL. Both CD4 and CD8 positive T cells were studied. Quadrant Q2 represent (%) T-cells positive for CD69 expressing and thus activated T-cells. Thus, it is demonstrated that oxCL but not CL can activate CD8-positive and CD4-positive T cells as determined by an increase in Q2 which is highly significant.

Figure 12:
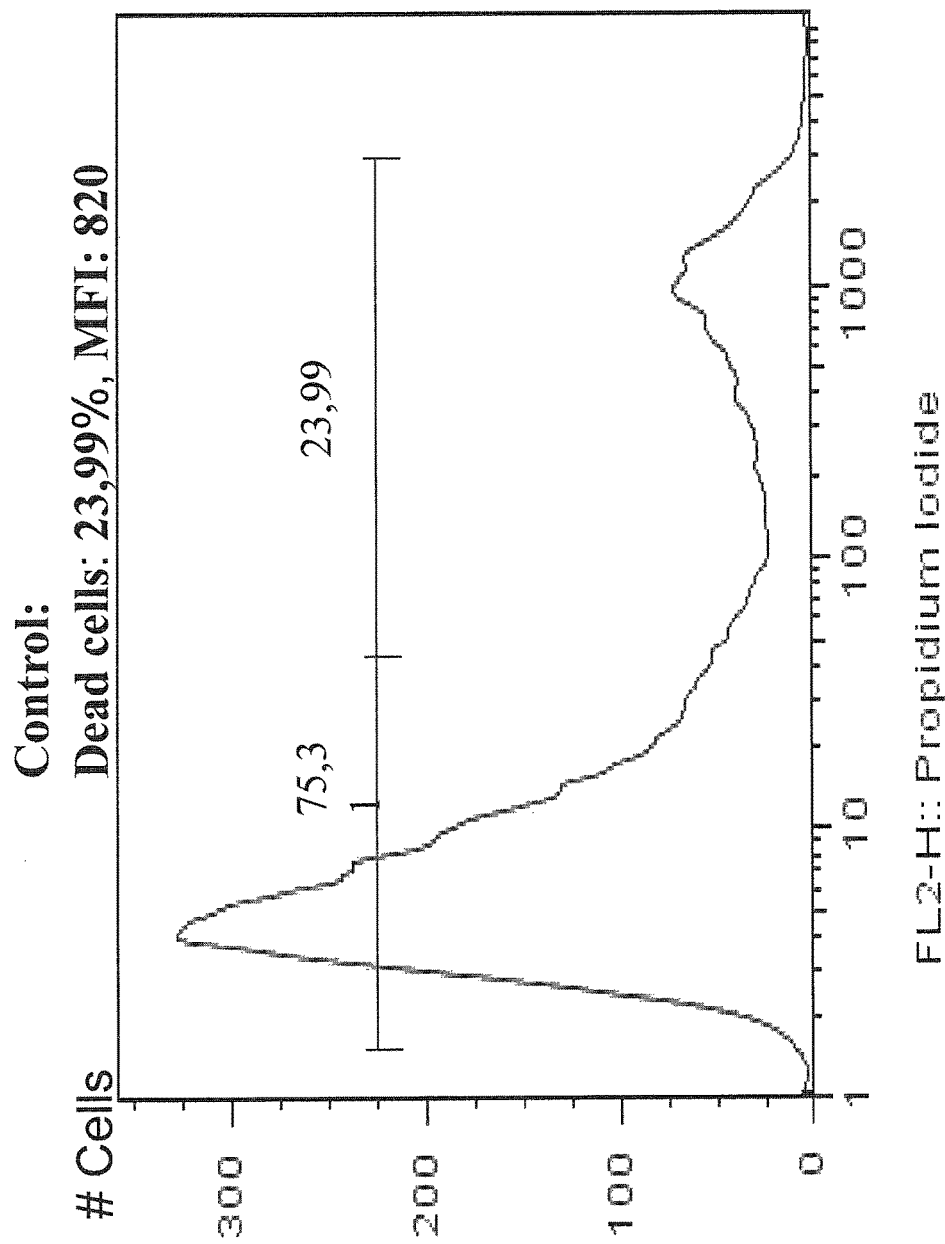
Figure 12:
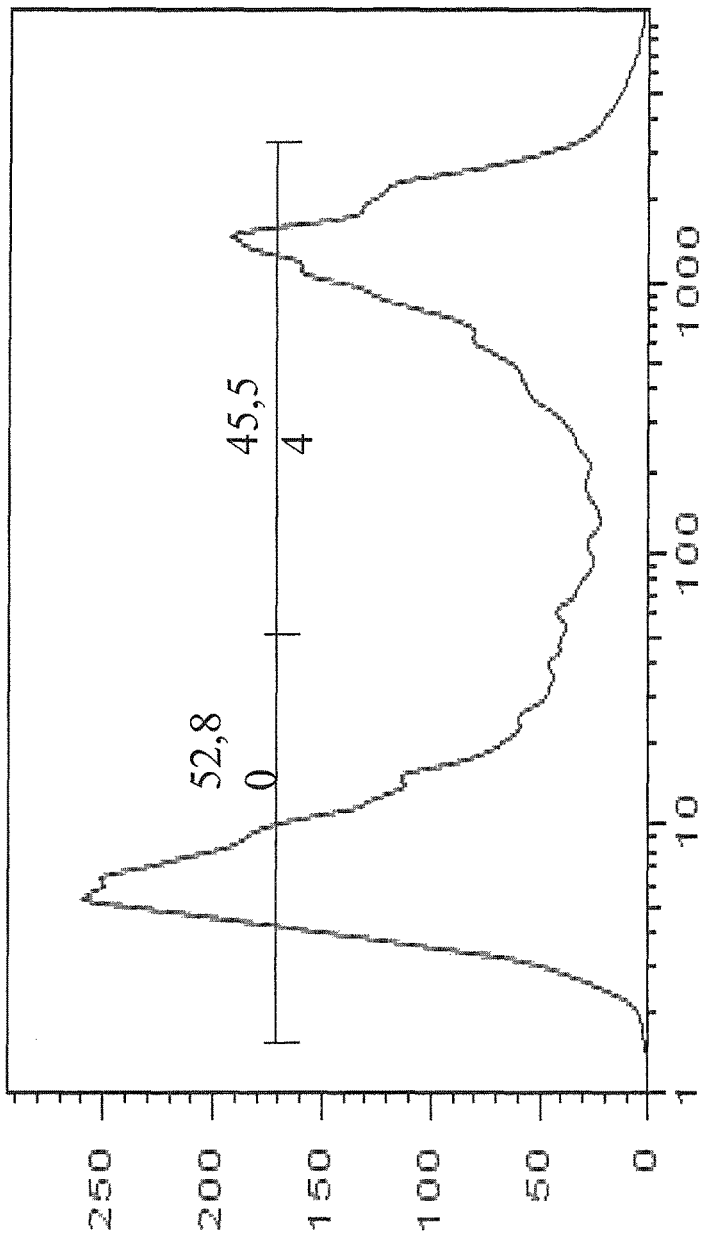
Figure 12:
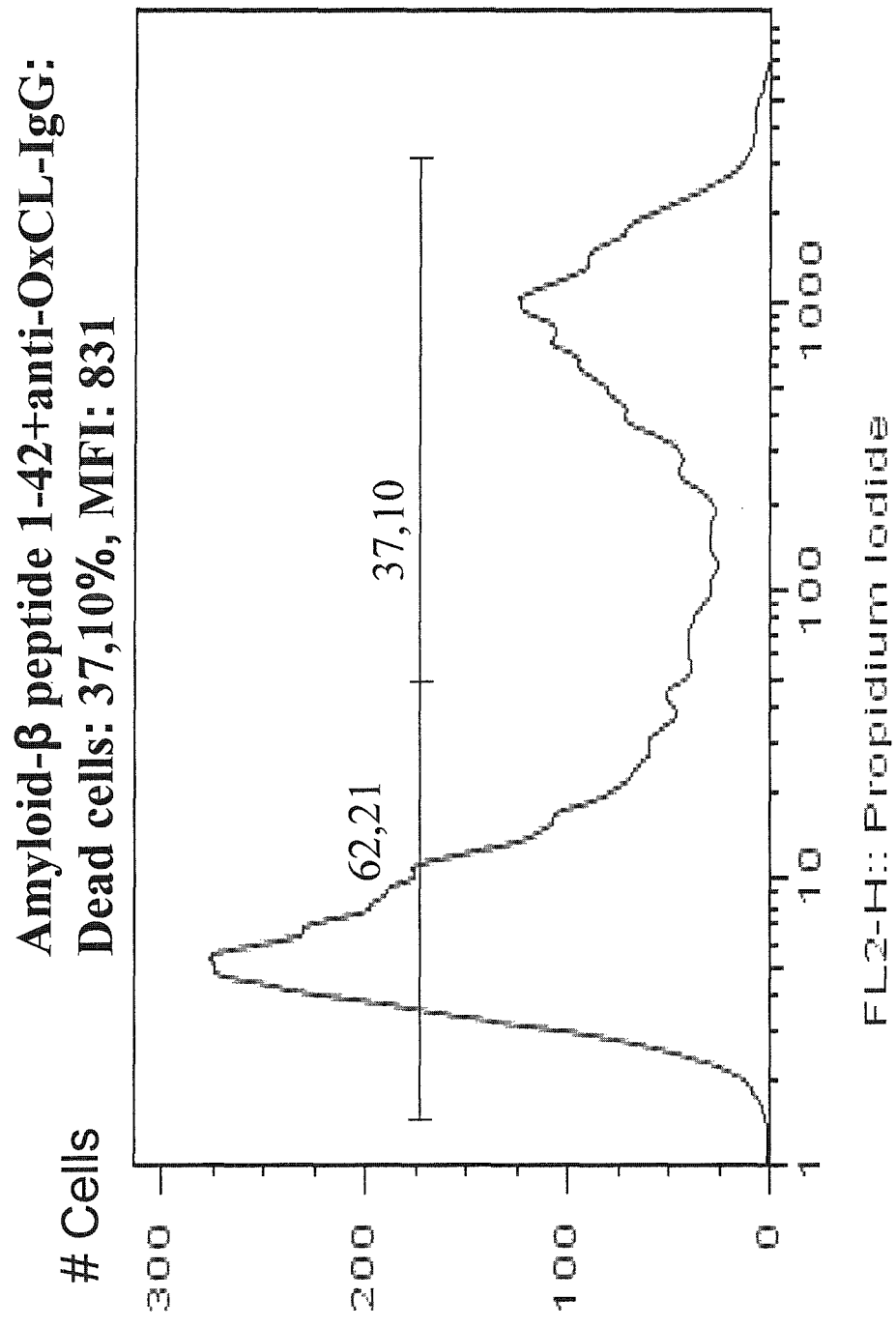

FIGS. 12A, 12B and 12C: A Neuroblastoma cell line was treated with amyloid peptide1-42 which induced cell death (as determined by propidium iodide; PI). Extracted anti-oxCL inhibited the effect.

EXAMPLE 1

Chemical Treatments of Cardiolipin

Native cardiolipin and oxidation product were further analyzed by mass spectrometry, FIGS. 1A and 1B. Native cardiolipin from bovine heart yielded two major signals, corresponding to the double charged anion (m/z 724.0), the single charged anion (m/z 1447). The oxidized derivative peaks from both double charged and single charged ions in the oxidized fraction were 8 m/z units apart, suggesting progressively oxidized cardiolipins.

EXAMPLE 2

Endothelial Cells and Adhesion Molecules

To study whether oxCL can stimulate endothelial cells to express adhesion molecules, HUVECs from passage 3 to 5 were incubated for 24 h with OxCL or native CL. Results suggested oxCL can significantly increase both ICAM-1 and VCAM-1 expression. But native CL did not show the same effect (FIGS. 2A and 2B). Both the increased expression of ICAM-1 and VCAM-1 (CD54 and CD106) induced by oxCL were significantly inhibited by Annexin A5 (FIGS. 3A and 3B).

EXAMPLE 3

IL-6 Production

10×6 HUVECs were seeded at 6 well plates. oxCL could stimulate endothelial cells produce 564.3±142.02 (pg/ml) IL-6 from the supernant. Annexin A5 significantly decreased II-6 level to 276.4±28.62 (pg/ml). Comparing with the control group, both native CL and Annexin A5 themselves could not significantly increase endothelial cell II-6 levels (FIG. 4). This supports the hypothesis that oxCL stimulates the IL-6, which is a known inflammatory marker, e.g. oxCL might be involved in inducing/mediating inflammatory responses.

EXAMPLE 4

Uptake Experiment

To study potential mechanisms of oxCL bioactivity, $1\times10^6$/well THP-1 differentiated macrophages (MQ) were used for uptake studies. oxLDL could inhibit dil-OxLDL uptake up to more than 60%, but LDL hade almost no effect on the uptake of dil-oxLDL which confirmed the specificity of uptake results. Further results suggested oxCL could in a concentration dependent manner inhibit dil-oxLDL uptake while the native CL did not show the competition effetcts (FIGS. 6A and 6B).

EXAMPLE 5

Intracellular Calcium Mobilization

To study the influence of oxCL on intracellular calcium mobilization, 5×104 neutrophil cells/well were used for measuring calcium mobilization. After adding oxCL, MFI of calcium mobilization in the cells were significantly increased within 120 seconds. This increase induced by oxCL was greatly inhibited by incubation of Annexin A5. But Annexin A5 and native CL did not increase calcium mobilization (FIG. 7A-7D).

EXAMPLE 6

LTB4 Production

Human mononuclear cells isolated from freshly prepared buffy coats were differentiated into macrophages according to protocols which are well known to those skilled in the art. $2\times10^6$ cells/well were exposed to OxCL, CL or buffer solution. Results suggested OxCL could in a concentration dependent manner induce LTB4 production but not with native CL (FIG. 8). This increase was greatly inhibited by Annexin A5 (FIG. 9).

EXAMPLE 7

ELISA for Annexin A5 Binding to Antigen

To test potential protective mechanisms of Annexin A5, oxCL, CL and reduced CL (5 ug/ml) were coated on ELISA plates overnight before different concentrations of Annexin A5 (0.32 ug/ml, 0.64 ug/ml, 1.28 ug/ml, 2.56 ug/ml, 5.12 ug/ml and 10.24 ug/ml) were added to plates. Results suggested that different concentration of Annexin A5 could bind to oxCL, which was also much stronger than overnights air exposed CL. Reduced CL could not bind to Annexin A5 (FIG. 5).

EXAMPLE 8

The Role of IgM Antibodies Against Oxidized Cardiolipin (Anti-oxCL) in Prediction of Cardiovascular Disease (CVD) by Use of ELISA Between Jul. 1, 1997 and Jun. 30, 1998, every third 60-year old man and woman, in the County of Stockholm, were invited to participate. The response rate was 78% and 4232 subjects (2039 men and 2193 women) were included. Information on sociodemography, lifestyle, medication and diseases was obtained by a self-administered questionnaire.

Physical examination (including blood pressure measurements, anthropometry and ECG) was performed and serum, plasma and whole blood were collected for storage (−80° C.). Routine tests were used for fasting levels of blood lipids (total cholesterol, HDL-cholesterol, LDL-cholesterol and triglycerides), apolipoproteins blood glucose, s-insulin, p-fibrinogen and hsCRP.

New events of coronary heart disease (CHD), myocardial infarction (MI), hospitalization for angina pectoris, ischemic stroke were registered. The study base of 4232 subjects was matched with that of the national cause of death registry (fatal events until Dec. 31, 2003) and the national in-hospital registry (non-fatal events until Dec. 31, 2005).

211 incident cases of CVD were recorded. Only subjects without a history of CVD prior to recruitment were utilized for the matching procedures. To assess diagnoses of CVD events, the International Classification of Diseases (ICD-10) was used to register CHD-deaths (I 20, I 21, I46), MI (I 21), angina pectoris including PCIs and CABGs (I 20, Z 95.5 and Z 95.1) and ischemic stroke (I 63-I 66). For each case three sex- and age-matched controls were randomly selected. Through this nested case-control design (211 cases and 633 controls) was applied to determine relative risks for future events.

The screening of 4232 subjects, 60-year-old (2039 men and 2193 women) with a follow up of 5-7 years was conducted and 211 incident cases of CVD (myocardial infarction, ischemic stroke, or hospitalized angina pectoris) and 633 age- and sex-matched controls were identified. Values were adjusted for smoking, BMI, type II diabetes, hypercholesterolaemia, and high blood pressure. An increased risk of CVD was determined as described in the tables.

Crude values include the matching factors age and sex. In addition adjustments have been made for smoking, BMI>29 kg/m², type II diabetes, high s-cholesterol≥5 mmol/l, high blood pressure >140/90 mmHg.

Descriptive analyses of were performed for cases and controls respectively with values expressed as medians (ranges) or proportions. Relative risks (RR) with 95% confidence intervals (CI) were calculated applying conditional logistic regressions. Analyses were run both crude and adjusted for traditional risk factors (as assessed by univariate analyses of significant differences between cases and controls). Statistical analyses were run with SAS®statistical software system version 9.1.

Thus, low anti-oxCL levels predicted a striking risk of stroke (CVD) and myocardial infarction (MI) in men, and also increased risk of myocardial infarction (MI) in women. It was not possible to study a similar effect of low anti-oxCL on the risk of stroke in woman due to a limited set of data.

Units were arbitrarily determined with sera two persons with moderately high-level anti-oxCL on each ELISA plate and these were used as controls and was the basis of Unit determinations. Quartile 4 represents the highest 25% of values in the whole cohort.

TABLE 1a

Association between low levels of anti-OxCL and risk for CVD, men and women

| aOxCL | Crude | | | Adjust | | |
|---|---|---|---|---|---|---|
| Quartiles | RR | 95% CI | P-values | RR | 95% CI | P-values |
| Quartile 4 | 1 | N/A | N/A | 1 | N/A | N/A |
| Quartile 3 | 1.66 | 0.97-2.85 | 0.0653 | 1.84 | 1.08-3.33 | 0.0267 |
| Quartile 2 | 1.67 | 0.97-2.88 | 0.0658 | 1.69 | 0.96-3.00 | 0.0699 |
| Quartile 1 | 2.15 | 1.25-3.70 | 0.0036 | 2.15 | 1.23-3.78 | 0.0075 |

TABLE 3a

Association between low levels of anti-OxCL and risk for MI, men

| aOxCL | Crude | | | Adjust | | |
|---|---|---|---|---|---|---|
| Quartiles | RR | 95% CI | P-values | RR | 95% CI | P-values |
| Quartile 4 | 1 | N/A | N/A | 1 | N/A | N/A |
| Quartile 3 | 1.39 | 0.73-2.66 | | 1.6 | 0.81-3.17 | |
| Quartile 2 | 1.51 | 0.78-2.94 | | 1.7 | 0.84-3.46 | |
| Quartile 1 | 2.16 | 1.14-4.09 | | 2.30 | 1.17-4.51 | |

TABLE 4

Association between low levels of anti-OxCL and risk for MI, women

| aOxCL | Crude | | | Adjust | | |
|---|---|---|---|---|---|---|
| Quartiles | RR | 95% CI | P-values | RR | 95% CI | P-values |
| Quartile 4 | 1 | N/A | N/A | 1 | N/A | N/A |
| Quartile 3 | 2.52 | 0.93-6.82 | | 2.96 | 1.05-8.30 | |
| Quartile 2 | 2.13 | 0.82-5.52 | | 1.97 | 0.73-5.31 | |
| Quartile 1 | 1.97 | 0.70-5.61 | | 1.87 | 0.65-5.41 | |

TABLE 5a

Association between low levels of anti-OxCL and risk for stroke, men

| aOxCL | Crude | | | Adjust | | |
|---|---|---|---|---|---|---|
| Quartiles | RR | 95% CI | P-values | RR | 95% CI | P-values |
| Quartile 4 | 1 | N/A | N/A | 1 | N/A | N/A |
| Quartile 3 | 2.24 | 0.54-9.31 | | 7.05 | 1.05-47.4 | |
| Quartile 2 | 2.7 | 0.54-13.48 | | 8.03 | 0.93-69.56 | |
| Quartile 1 | 2.69 | 0.64-11.31 | | 12.28 | 1.48-101.77 | |

Relative risks (RR) using SAS were determined with 95% confidence intervals (CI) and quartiles of anti-oxCL levels where the 100% percentile was set as the reference value (RR=1.0). Thus, the percentile unit represent the indicated fraktile of the level of anti-oxCL of the analysed patients, respectively. Cut off levels are based on the total of men and women.

Thus, low anti-oxCL levels predicted a striking risk of stroke (CVD) and myocardial infarction, MI, in men, and also increased risk of myocardial infarction, MI, in women. It was not possible to have a similar effect of low anti-oxCL on the risk of stroke in woman confirmed due to a limited set of data].

In the following tables in this example, levels below the indicated were compared to those above.

TABLE 7a

Association between low levels of anti-OxCL and risk for cvd men + women

| aOxCL percentile unit | Crude | | | Adjust | | |
|---|---|---|---|---|---|---|
| | RR | 95% CI | P-values | RR | 95% CI | P-values |
| 35 | 1.499 | 1.077 2.086 | 0.0163 | 1.520 | 1.076 2.146 | 0.0174 |
| 33 | 1.487 | 1.067 2.073 | 0.0191 | 1.484 | 1.049 2.099 | 0.0256 |
| 30 | 1.408 | 1.006 1.971 | 0.0460 | 1.386 | 0.976 1.968 | 0.0684 |
| 25 | 1.361 | 0.951 1.949 | 0.0919 | 1.366 | 0.941 1.982 | 0.1010 |
| 24 | 1.206 | 0.838 1.735 | 0.3136 | 1.219 | 0.836 1.776 | 0.3034 |
| 23 | 1.168 | 0.808 1.686 | 0.4086 | 1.185 | 0.810 1.733 | 0.3826 |
| 22 | 1.129 | 0.779 1.636 | 0.5220 | 1.145 | 0.781 1.677 | 0.4882 |
| 21 | 1.204 | 0.831 1.745 | 0.3253 | 1.219 | 0.831 1.787 | 0.3111 |
| 20 | 1.280 | 0.876 1.870 | 0.2018 | 1.282 | 0.867 1.895 | 0.2137 |
| 19 | 1.345 | 0.915 1.978 | 0.1315 | 1.333 | 0.896 1.983 | 0.1559 |
| 18 | 1.493 | 1.012 2.202 | | 1.480 | 0.991 2.211 | 0.0556 |
| 17 | 1.400 | 0.938 2.090 | 0.0993 | 1.379 | 0.913 2.082 | 0.1265 |
| 16 | 1.385 | 0.915 2.097 | 0.1235 | 1.363 | 0.891 2.085 | 0.1531 |
| 15 | 1.410 | 0.924 2.151 | 0.1108 | 1.386 | 0.901 2.132 | 0.1377 |
| 14 | 1.527 | 0.988 2.360 | 0.0568 | 1.511 | 0.969 2.357 | 0.0688 |
| 13 | 1.620 | 1.040 2.524 | 0.0330 | 1.556 | 0.989 2.446 | 0.0558 |

TABLE 8a

Association between low levels of anti-OxCL and risk for cvd men

| aOxCL percentile unit | Crude | | | Adjust | | |
|---|---|---|---|---|---|---|
| | RR | 95% CI | P-values | RR | 95% CI | P-values |
| 35 | 1.936 | 1.295 2.896 | 0.0013 | 2.050 | 1.342 3.133 | 0.0009 |
| 33 | 2.027 | 1.355 3.033 | 0.0006 | 2.142 | 1.401 3.274 | 0.0004 |
| 30 | 1.801 | 1.201 2.700 | 0.0044 | 1.885 | 1.232 2.884 | 0.0035 |
| 25 | 1.594 | 1.047 2.427 | 0.0296 | 1.655 | 1.067 2.566 | 0.0244 |
| 24 | 1.401 | 0.913 2.148 | 0.1224 | 1.440 | 0.924 2.246 | 0.1073 |
| 23 | 1.357 | 0.882 2.087 | 0.1648 | 1.412 | 0.903 2.208 | 0.1305 |
| 22 | 1.265 | 0.819 1.954 | 0.2895 | 1.311 | 0.837 2.053 | 0.2369 |
| 21 | 1.347 | 0.873 2.078 | 0.1777 | 1.389 | 0.887 2.174 | 0.1511 |
| 20 | 1.412 | 0.910 2.189 | 0.1235 | 1.460 | 0.927 2.299 | 0.1026 |
| 19 | 1.448 | 0.927 2.262 | 0.1037 | 1.479 | 0.932 2.346 | 0.0966 |
| 18 | 1.618 | 1.031 2.539 | 0.0362 | 1.638 | 1.026 2.613 | 0.0386 |
| 17 | 1.519 | 0.958 2.409 | 0.0754 | 1.507 | 0.937 2.424 | 0.0909 |
| 16 | 1.570 | 0.973 2.533 | 0.0646 | 1.560 | 0.955 2.549 | 0.0760 |
| 15 | 1.522 | 0.935 2.476 | 0.0910 | 1.485 | 0.903 2.442 | 0.1192 |
| 14 | 1.620 | 0.980 2.677 | 0.0598 | 1.591 | 0.952 2.660 | 0.0763 |
| 13 | 1.839 | 1.104 3.062 | 0.0193 | 1.731 | 1.028 2.915 | 0.0392 |

TABLE 9a

Association between low levels of anti-OxCL and risk for MI men

| aOxCL percentile unit | Crude | | | Adjust | | |
|---|---|---|---|---|---|---|
| | RR | 95% CI | P-values | RR | 95% CI | P-values |
| 35 | 1.895 | 1.213 2.960 | 0.0050 | 1.912 | 1.191 3.069 | 0.0073 |
| 33 | 2.005 | 1.283 3.133 | 0.0023 | 2.023 | 1.259 3.250 | 0.0036 |
| 30 | 1.852 | 1.178 2.909 | 0.0075 | 1.829 | 1.135 2.947 | 0.0132 |
| 25 | 1.652 | 1.032 2.643 | 0.0363 | 1.609 | 0.980 2.642 | 0.0602 |
| 24 | 1.508 | 0.936 2.429 | 0.0912 | 1.460 | 0.884 2.413 | 0.1396 |
| 23 | 1.431 | 0.884 2.318 | 0.1449 | 1.409 | 0.846 2.347 | 0.1882 |
| 22 | 1.290 | 0.792 2.103 | 0.36 | 1.274 | 0.764 2.124 | 0.3525 |
| 21 | 1.397 | 0.859 2.270 | 0.1777 | 1.361 | 0.816 2.268 | 0.2376 |
| 20 | 1.484 | 0.906 2.431 | 0.1169 | 1.442 | 0.859 2.422 | 0.1661 |
| 19 | 1.477 | 0.895 2.438 | 0.1270 | 1.426 | 0.844 2.409 | 0.1851 |
| 18 | 1.614 | 0.978 2.663 | 0.0610 | 1.545 | 0.911 2.620 | 0.1062 |
| 17 | 1.561 | 0.937 2.599 | 0.0873 | 1.470 | 0.862 2.509 | 0.1575 |
| 16 | 1.589 | 0.935 2.701 | 0.0871 | 1.511 | 0.870 2.622 | 0.1426 |
| 15 | 1.529 | 0.889 2.630 | 0.1249 | 1.433 | 0.817 2.513 | 0.2097 |
| 14 | 1.658 | 0.954 2.882 | 0.0729 | 1.574 | 0.887 2.794 | 0.1212 |
| 13 | 1.895 | 1.080 3.327 | 0.0260 | 1.724 | 0.959 3.098 | 0.0685 |

TABLE 10a

Association between low levels of anti-OxCL and risk for stroke men

| aOxCL percentile unit | Crude | | | Adjust | | |
|---|---|---|---|---|---|---|
| | RR | 95% CI | P-values | RR | 95% CI | P-values |
| 35 | 2.127 | 0.833 5.430 | 0.1143 | 4.031 | 1.107 14.674 | 0.0345 |
| 33 | 2.127 | 0.833 5.430 | 0.1143 | 4.031 | 1.107 14.674 | 0.0345 |
| 30 | 1.607 | 0.645 4.003 | | 3.410 | 0.942 12.347 | 0.0617 |
| 25 | 1.385 | 0.543 3.531 | 0.4950 | 2.453 | 0.719 8.376 | 0.1521 |
| 24 | 1.042 | 0.397 2.735 | 0.9342 | 1.712 | 0.497 5.898 | 0.3941 |
| 23 | 1.104 | 0.426 2.866 | 0.8382 | 1.762 | 0.521 5.962 | 0.3622 |
| 22 | 1.174 | 0.452 3.051 | 0.7421 | 1.882 | 0.553 6.406 | 0.3118 |
| 21 | 1.174 | 0.452 3.051 | 0.7421 | 1.882 | 0.553 6.406 | 0.3118 |
| 20 | 1.174 | 0.452 3.051 | 0.7421 | 1.882 | 0.553 6.406 | 0.3118 |
| 19 | 1.344 | 0.506 3.565 | 0.5531 | 2.123 | 0.611 7.372 | 0.2358 |
| 18 | 1.637 | 0.584 4.588 | 0.3488 | 2.246 | 0.638 7.907 | 0.2078 |
| 17 | 1.352 | 0.465 3.933 | 0.5802 | 1.704 | 0.474 6.125 | 0.4145 |
| 16 | 1.491 | 0.495 4.490 | 0.4772 | 1.86 | 0.506 7.095 | 0.3423 |
| 15 | 1.491 | 0.495 4.490 | 0.4772 | 1.896 | 0.506 7.095 | 0.3423 |
| 14 | 1.454 | 0.441 4.792 | 0.5388 | 1.566 | 0.388 6.321 | 0.5290 |
| 13 | 1.605 | 0.486 5.306 | 0.4379 | 1.649 | 0.427 6.371 | 0.4679 |

EXAMPLE 9

The same data material as described in example 8 was used herein.

Descriptive analyses were performed for cases and controls respectively with values expressed as medians (ranges) or proportions. Relative risks (RR) with 95% confidence intervals (CI) were calculated applying conditional logistic regressions. Analyses were run both crude and adjusted for traditional risk factors (as assessed by univariate analyses of significant differences between cases and controls). Statistical analyses were run with SAS®statistical software system version 9.1.

Relative risks (RR) using SAS were determined with 95% confidence intervals (CI) and quartiles of anti-oxCL levels where the highest quartile representing the highest values of anti-OxCL was set as the reference value (RR=1.0). Thus, percentile units represent the 76% and up to 98% fraktile of the level of anti-oxCL of the analysed patients, respectively. Cut off levels are based on the total of men and women.

Thus, low levels of anti-OxCL are associated with increased risk of development of CVD. Here it is demonstrated that high levels of anti-OxCL can be protective for CVD.

Association Between High Levels of Anti-OxCL and Risk for CVD (MI-stroke)Men+Women

| aOxCL percentile unit | Crude | | | Adjust | | |
|---|---|---|---|---|---|---|
| | RR | 95% CI | P-values | RR | 95% CI | P-values |
| 98 | 0.693 | 0.197 2.430 | 0.5662 | 0.566 | 0.154 2.078 | 0.3912 |
| 96 | 0.825 | 0.354 1.924 | 0.6564 | 0.716 | 0.297 1.722 | 0.4550 |
| 94 | 0.649 | 0.310 1.360 | 0.2522 | 0.606 | 0.283 1.296 | 0.1966 |
| 90 | 0.631 | 0.351 1.134 | 0.1239 | 0.600 | 0.331 1.089 | 0.0929 |
| 86 | 0.537 | 0.319 0.905 | 0.0196 | 0.485 | 0.283 0.829 | 0.0082 |
| 84 | 0.576 | 0.356 0.932 | 0.0246 | 0.534 | 0.326 0.874 | 0.0125 |
| 82 | 0.607 | 0.387 0.950 | 0.0291 | 0.577 | 0.365 0.913 | 0.0187 |
| 80 | 0.698 | 0.460 1.057 | 0.0892 | 0.653 | 0.427 1.001 | 0.0503 |
| 78 | 0.734 | 0.493 1.092 | 0.1272 | 0.706 | 0.469 1.062 | 0.0946 |
| 76 | 0.661 | 0.443 0.986 | 0.0425 | 0.643 | 0.427 0.969 | 0.0347 |

Association Between High Levels of Anti-OxCL and Risk for CVD (MI-stroke)Men

| aOxCL percentile unit | Crude | | | Adjust | | |
|---|---|---|---|---|---|---|
| | RR | 95% CI | P-values | RR | 95% CI | P-values |
| 98 | 0.750 | 0.159 3.532 | 0.7161 | 0.522 | 0.104 2.625 | 0.4301 |
| 96 | 0.918 | 0.336 2.507 | 0.8672 | 0.705 | 0.245 2.024 | 0.5155 |
| 94 | 0.648 | 0.264 1.592 | 0.3438 | 0.539 | 0.211 1.375 | 0.1959 |
| 90 | 0.415 | 0.182 0.949 | 0.0371 | 0.364 | 0.157 0.843 | 0.0184 |
| 86 | 0.425 | 0.211 0.858 | 0.0170 | 0.359 | 0.174 0.743 | 0.0057 |
| 84 | 0.421 | 0.215 0.821 | 0.0112 | 0.358 | 0.179 0.712 | 0.0035 |
| 82 | 0.473 | 0.258 0.868 | 0.0156 | 0.421 | 0.225 0.787 | 0.0067 |
| 80 | 0.578 | 0.334 1.001 | 0.0505 | 0.518 | 0.293 0.914 | 0.0232 |
| 78 | 0.607 | 0.361 1.020 | 0.0594 | 0.565 | 0.330 0.968 | 0.0377 |
| 76 | 0.534 | 0.315 0.905 | 0.0197 | 0.496 | 0.286 0.858 | 0.0121 |

Association Between High Levels of Anti-OxCL and Risk for CVD (Infakt-stroke)Women

| aOxCL percentile unit | Crude | | | Adjust | | |
|---|---|---|---|---|---|---|
| | RR | 95% CI | P-values | RR | 95% CI | P-values |
| 98 | 0.600 | 0.070 5.136 | 0.6410 | 0.612 | 0.067 5.572 | 0.6628 |
| 96 | 0.652 | 0.136 3.133 | 0.5930 | 0.696 | 0.136 3.570 | 0.6641 |
| 94 | 0.653 | 0.178 2.391 | 0.5194 | 0.746 | 0.195 2.851 | 0.6688 |
| 90 | 1.121 | 0.475 2.643 | 0.7944 | 1.170 | 0.483 2.836 | 0.7280 |
| 86 | 0.756 | 0.343 1.663 | 0.4861 | 0.716 | 0.317 1.619 | 0.4222 |
| 84 | 0.878 | 0.430 1.793 | 0.7215 | 0.905 | 0.435 1.881 | 0.7889 |
| 82 | 0.865 | 0.439 1.702 | 0.6737 | 0.878 | 0.439 1.757 | 0.7136 |
| 80 | 0.924 | 0.486 1.755 | 0.8083 | 0.893 | 0.462 1.727 | 0.7371 |
| 78 | 0.992 | 0.530 1.856 | 0.9788 | 0.967 | 0.510 1.833 | 0.9179 |
| 76 | 0.919 | 0.491 1.719 | 0.7921 | 0.911 | 0.484 1.717 | 0.7739 |

EXAMPLE 10

Patient sera from a women control population was used herein. Data was obtained by use of simple regression and Spearman Rank test was used in statistical analysis (Stat View).

The association between important parameters and determinants in relation to anti-oxCL oxCL is determined.

Controls from the General Population (Population Controls; 26 Women)

| Clinical role of antibodies against oxidized cardiolipin and | R | p |
|---|---|---|
| Glucos in plasma | −0.41 | 0.035 |
| Systolic blood pressure | −0.66 | 0.001 |
| Diastolic blood pressure | −0.428 | 0.015 |
| Age no association | | 0.2 |
| BMI | −0.56 | 0.0053 |

No association with anticardiolipin antibodies or lupus antikoagulans (an indirect measure for anti-cardiolipin antibodies): p=0.41

Thus, these data indicate strong and significant negative associations between anti-OxCL antibodies and important factors as blood pressure, diabetes and blood sugar, Body Mass Index and a positive association with endothelial function. One mechanism can be oxCL-effects on endothelium, causing endothelial activation and dysfunction if protective anti-oxCL are low.

The role of anti-oxCL in 52 women with a prototypic autoimmune disorder, systemic lupus erythematosus (SLE) is demonstrated.

SLE-Patients: Association Between Anti-OxCL in Women with SLE (n=52)

| Clinical role of antibodies against oxidized cardiolipin and | R | P |
|---|---|---|
| TNF-induction when leukocytes (PBMC) are cultured with endotoxin 1 ng/ml and serum from patients | −0.32 | 0.02. |
| Endothelial function (nitroinduced dilatation of a Brachialis) | 0.43 | 0.023 |
| VCAM (important inflammatory/vascular marker): | −0.40 | 0.0046 |
| TNF (Major inflammatory cytokine) | −0.40 | 0.0043 |
| Age no association | | 0.89 |

DIsease severity index SLICC: below index 4 (117 ± 48 compared to above index 4 (63 ± 14); p = 0.0085

Thus, strong negative association between major SLE measures and inflammation and anti-OxCL exists. In the prototypic autoimmune disease SLE, a strong negative association between anti-oxCL on the one hand and TNF-induction and other inflammatory markers, is determined, indicating an anti-inflammatory role played by these antibodies. Further, there is a positive association with endothelial function, indicating a positive effect which also has implications for cardiovascular disease. A specific potential role in SLE-manifestations and disease severity is demonstrated by an association with SLICC, an index of disease damage, where higher anti-OxCL could ameliorate disease.

EXAMPLE 11

Both CD4 and CD8 positive T-cells from the cell line Human PBMC where studied in an incubation setup illustrated in FIG. 11A-F. Both T-cell types where incubated with, buffer (control), oxCL or CL to determine the effect on activation, interpreted by the expression of CD69 surface molecule after stimulation.

In this experiment the attention must be drawn to the quadrant Q2 of the flow cytometry data shown. This quadrant represents the percentage of T-cells in the population tested to be CD69 positive, e.g. activated by the stimuli prior to the data collection.

The control-stimulation (FIGS. 11A and D), without CL or oxCL, no induction of CD69 expression was detected in CD4 or CD8 positive lymphocytes. The same is true for the population of T-cells treated with CL (FIGS. 11C and F) before measuring the CD69 expression, represented by very similar data plots. However, the expression of CD69 was notably elevated in oxCL stimulated T-cells positive for CD4 and CD8 (FIGS. 11B and E). A distinct shift from quadrant Q1 to Q2 is seen when comparing data from the control and CL-experiment to the oxCL-data.

This experiment shows that an immune response can be induced by oxCL, indicated by the oxCL, but not CL mediated expression of CD69 on the surface of CD4 and CD8 positive T-cells.

FIG. 12A-C illustrates the effect of anti-oxCL on amyloid peptide 1-42 induced cell death.

The beta amyloid (Abeta) and especially Abeta peptide (1-42), is an important component of senile plaques in Alzheimer's disease, and is known to be directly responsible for the production of free radicals toxic to brain tissue. Abeta(1-42)-induced free radical oxidative stress in the neurodegeneration observed in AD brain may be one mechanism for neurotoxicity. Human SH-SY5Y neuroblastoma cells were used in cell culture systems.

The cells were treated with 5 uM of the peptide for 24 hours. Cell death was determined by the addition of 1 mg/mL propidium iodide (PI), which labels the nucleus in dying cells which lack an intact plasma membrane.

In the control experiment the amount of dead cells was measured to 23,99%, whereas the amlyoid peptide 1-42 induced cell death increased that number to 45,54%. When amyloid peptide1-42 was incubated together with oxCL-IgG, 30 ug/ml, (anti-oxCL), the cell dead is reduced to 37,10%.

This experiment confirms that anti oxCL will have a protective effect on cell death induced by the amyloid peptide 1-42. Thus, this supports the notion that anti-OxCL can have a protective effect against Alzheimer.

Thus, from the above it emerges, that oxCL has a T-cell activating properties, and is involved in cell death, which is supported by the cell death protective effect of anti-oxCL illustrated in FIG. 12A-C.

REFERENCES

1. Schlame M. Cardiolipin synthesis for the assembly of bacterial and mitochondrial membranes. *J Lipid Res.* 2008;49:1607-20.
2. Martin W, Hoffmeister M, Rotte C, Henze K. An overview of endosymbiotic models for the origins of eukaryotes, their ATP-producing organelles (mitochondria and hydrogenosomes), and their heterotrophic lifestyle. *Biol. Chem.* 2001;382:1521-39.
3. Deguchi H, Fernandez J A, Hackeng T M, Banka C L, Griffin J H. Cardiolipin is a normal component of human plasma lipoproteins. *Proc Natl Acad Sci USA.* 2000;97:1743-8.
4. Schlame M, Rua D, Greenberg M L. The biosynthesis and functional role of cardiolipin. *Prog Lipid Res.* 2000;39:257-88.
5. Chicco A J, Sparagna G C. Role of cardiolipin alterations in mitochondrial dysfunction and disease. *Am J Physiol Cell Physiol.* 2007;292:C33-44.
6. Belikova N A, Jiang J, Tyurina Y Y, Zhao Q, Epperly M W, Greenberger J, Kagan V E. Cardiolipin-specific peroxidase reactions of cytochrome C in mitochondria during irradiation-induced apoptosis. *Int J Radiat Oncol Biol Phys.* 2007;69:176-86.
7. Basova L V, Kurnikov I V, Wang L, Ritov V B, Belikova N A, Vlasova, I I, Pacheco A A, Winnica D E, Peterson J, Bayir H, Waldeck D H, Kagan V E. Cardiolipin switch in mitochondria: shutting off the reduction of cytochrome c and turning on the peroxidase activity. *Biochemistry.* 2007;46:3423-34.
8. Gonzalvez F, Gottlieb E. Cardiolipin: setting the beat of apoptosis. *Apoptosis.* 2007;12:877-85.
9. Nakagawa Y. Initiation of apoptotic signal by the peroxidation of cardiolipin of mitochondria. *Ann N Y Acad Sci.* 2004;1011:177-84.
10. Frostegard J. Atherosclerosis in patients with autoimmune disorders. *Arterioscler Thromb Vasc Biol.* 2005;25:1776-85.
11. Hamsten A, Norberg R, Bjorkholm M, de Faire U, Holm G. Antibodies to cardiolipin in young survivors of myocardial infarction: an association with recurrent cardiovascular events. *Lancet.* 1986;1:113-6.
12. Cederholm A, Svenungsson E, Jensen-Urstad K, Trollmo C, Ulfgren A K, Swedenborg J, Fei G Z, Frostegard J. Decreased binding of annexin v to endothelial cells: a potential mechanism in atherothrombosis of patients with systemic lupus erythematosus. *Arterioscler Thromb Vasc Biol.* 2005;25:198-203.
13. Vaarala O, Alfthan G, Jauhiainen M, Leirisalo-Repo M, Aho K, Palosuo T. Crossreaction between antibodies to oxidised low-density lipoprotein and to cardiolipin in systemic lupus erythematosus. *Lancet.* 1993;341:923-5.
14. Hansson G K. Inflammation, atherosclerosis, and coronary artery disease. *N Engl J. Med.* 2005;352:1685-95.
15. Frostegard J, Ulfgren A K, Nyberg P, Hedin U, Swedenborg J, Andersson U, Hansson G K. Cytokine expression in advanced human atherosclerotic plaques: dominance of pro-inflammatory (Th1) and macrophage-stimulating cytokines. *Atherosclerosis.* 1999; 145:33-43.
16. Funk C D. Leukotriene modifiers as potential therapeutics for cardiovascular disease. *Nat Rev Drug Discov.* 2005;4:664-72.
17. Yokomizo T, Izumi T, Chang K, Takuwa Y, Shimizu T. A G-protein-coupled receptor for leukotriene B4 that mediates chemotaxis. *Nature.* 1997;387:620-4.
18. Yokomizo T, Kato K, Terawaki K, Izumi T, Shimizu T. A second leukotriene B(4) receptor, BLT2. A new therapeutic target in inflammation and immunological disorders. *J Exp Med.* 2000;192:421-32.
19. Serezani C H, Aronoff D M, Jancar S, Mancuso P, Peters-Golden M. Leukotrienes enhance the bactericidal activity of alveolar macrophages against *Klebsiella pneumoniae* through the activation of NADPH oxidase. *Blood.* 2005;106:1067-75.
20. Wan M, Sabirsh A, Wetterholm A, Agerberth B, Haeggstrom J Z. Leukotriene B4 triggers release of the cathelicidin LL-37 from human neutrophils: novel lipid-peptide interactions in innate immune responses. *Faseb J.* 2007;21:2897-905.
21. Goodarzi K, Goodarzi M, Tager A M, Luster A D, von Andrian U H. Leukotriene B4 and BLT1 control cytotoxic effector T cell recruitment to inflamed tissues. *Nat. Immunol.* 2003;4:965-73.
22. Qiu H, Gabrielsen A, Agardh H E, Wan M, Wetterholm A, Wong C H, Hedin U, Swedenborg J, Hansson G K, Samuelsson B, Paulsson-Berne G, Haeggstrom J Z. Expression of 5-lipoxygenase and leukotriene A4 hydrolase in human atherosclerotic lesions correlates with symptoms of plaque instability. *Proc Natl Acad Sci USA.* 2006;103:8161-6.
23. Febbraio M, Podrez E A, Smith J D, Hajjar D P, Hazen S L, Hoff H F, Sharma K, Silverstein R L. Targeted disruption of the class B scavenger receptor CD36 protects against atherosclerotic lesion development in mice. *J Clin Invest.* 2000;105:1049-56.
24. Moore K J, Freeman M W. Scavenger receptors in atherosclerosis: beyond lipid uptake. *Arterioscler Thromb Vasc Biol.* 2006;26:1702-11.
25. Rand J H, Wu X X. Antibody-mediated disruption of the annexin-V antithrombotic shield: a new mechanism for thrombosis in the antiphospholipid syndrome. *Thromb Haemost.* 1999;82:649-55.
26. Cederholm A, Frostegard J. Annexin A5 in cardiovascular disease and systemic lupus erythematosus. *Immunobiology.* 2005;210:761-8.
27. Thiagarajan P, Benedict C R. Inhibition of arterial thrombosis by recombinant annexin V in a rabbit carotid artery injury model. *Circulation.* 1997;96:2339-47.
28. Ishii H, Hiraoka M, Tanaka A, Shimokado K, Yoshida M. Recombinant Annexin-2 inhibits the progress of diabetic nephropathy in a diabetic mouse model via recovery of hypercoagulability. *Thromb Haemost.* 2007;97:124-8.
29. Han X, Yang J, Yang K, Zhao Z, Abendschein D R, Gross R W. Alterations in myocardial cardiolipin content and composition occur at the very earliest stages of diabetes: a shotgun lipidomics study. *Biochemistry.* 2007; 46:6417-28.
30. Sparagna G C, Chicco A J, Murphy R C, Bristow M R, Johnson C A, Rees M L, Maxey M L, McCune S A, Moore R L. Loss of cardiac tetralinoleoyl cardiolipin in human and experimental heart failure. *J Lipid Res.* 2007; 48:1559-70.
31. Schlame M, Towbin J A, Heerdt P M, Jehle R, DiMauro S, Blanck T J. Deficiency of tetralinoleoyl-cardiolipin in Barth syndrome. *Ann Neurol.* 2002;51:634-7.
32. Horkko S, Miller E, Dudl E, Reaven P, Curtiss L K, Zvaifler N J, Terkeltaub R, Pierangeli S S, Branch D W, Palinski W, Witztum J L. Antiphospholipid antibodies are directed against epitopes of oxidized phospholipids. Recognition of cardiolipin by monoclonal antibodies to epitopes of oxidized low density lipoprotein. *J Clin Invest.* 1996;98:815-25.
33. Winyard P G, Tatzber F, Esterbauer H, Kus M L, Blake D R, Morris C J. Presence of foam cells containing oxidised low density lipoprotein in the synovial membrane from patients with rheumatoid arthritis. *Ann Rheum Dis.* 1993;52:677-80.
34. Frostegard J, Svenungsson E, Wu R, Gunnarsson I, Lundberg I E, Klareskog L, Horkko S, Witztum J L. Lipid peroxidation is enhanced in patients with systemic lupus erythematosus and is associated with arterial and renal disease manifestations. *Arthritis Rheum.* 2005;52:192-200.
35. Sjöberg B G. *Atherosclerosis.* 2008.
36. Tuominen A, Miller Y I, Hansen L F, Kesaniemi Y A, Witztum J L, Horkko S. A natural antibody to oxidized cardiolipin binds to oxidized low-density lipoprotein, apoptotic cells, and atherosclerotic lesions. *Arterioscler Thromb Vasc Biol.* 2006;26:2096-102.

All given references as listed above and discussed in the description are hereby incorporated by reference.

The invention claimed is:

1. A method of treating or reducing the risk of developing arthritis in a mammal, comprising administering to the mammal in need thereof a therapeutically effective amount of Annexin A5, wherein the arthritis is osteoarthritis or psoriatic arthritis.

2. The method according to claim 1, wherein the arthritis is osteoarthritis.

3. The method according to claim 2, wherein the mammal is selected from the group consisting of mice, rats, rabbits, dogs, cats, cattle, horses and humans.

4. The method according to claim 3, wherein the mammal is a horse.

5. The method according to claim 3, wherein the mammal is a dog.

6. The method according to claim 3, wherein the mammal is a human.

7. The method according to claim 2, wherein the Annexin A5 is in combination with any suitable adjuvants.

8. The method according to claim 1, wherein the arthritis is psoriatic arthritis.

9. The method according to claim 8, wherein the mammal is selected from the group consisting of mice, rats, rabbits, dogs, cats, cattle, horses and humans.

10. The method according to claim 9, wherein the mammal is a horse.

11. The method according to claim 9, wherein the mammal is a dog.

12. The method according to claim 9, wherein the mammal is a human.

13. The method according to claim 8, wherein the Annexin A5 is in combination with any suitable adjuvants.

14. The method according to claim 1, wherein the mammal is selected from the group consisting of mice, rats, rabbits, dogs, cats, cattle, horses and humans.

15. The method according to claim 14, wherein the mammal is a horse.

16. The method according to claim 14, wherein the mammal is a dog.

17. The method according to claim 14, wherein the mammal is a human.

18. The method according to claim 1, wherein the Annexin A5 is in combination with any suitable adjuvants.

* * * * *